United States Patent [19]

Groman et al.

[11] Patent Number: 4,951,675
[45] Date of Patent: * Aug. 28, 1990

[54] BIODEGRADABLE SUPERPARAMAGNETIC METAL OXIDES AS CONTRAST AGENTS FOR MR IMAGING

[75] Inventors: Ernest V. Groman, Brookline; Lee Josephson, Arlington; Jerome M. Lewis, Newton, all of Mass.

[73] Assignee: Advanced Magnetics, Incorporated, Cambridge, Mass.

[ * ] Notice: The portion of the term of this patent subsequent to Sep. 13, 2005 has been disclaimed.

[21] Appl. No.: 244,432

[22] Filed: Sep. 14, 1988

Related U.S. Application Data

[60] Division of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^5$ .................................................. A61B 6/00
[52] U.S. Cl. ................................ 128/653 C A; 424/9; 600/12
[58] Field of Search ........ 128/654, 653, 714, 897–899; 424/1.1, 4, 9, 173, 809; 600/1, 3, 12

[56] References Cited

U.S. PATENT DOCUMENTS

Re. 27,240  11/1971  London et al. .

(List continued on next page.)

FOREIGN PATENT DOCUMENTS

| 0184899 | 6/1985 | European Pat. Off. . |
|---|---|---|
| 0160552 | 11/1985 | European Pat. Off. . |
| 0186947 | 7/1986 | European Pat. Off. . |
| 3443252 | 5/1986 | Fed. Rep. of Germany . |
| 0186616 | 7/1986 | Fed. Rep. of Germany . |
| 13098 | 9/1956 | Japan . |
| 45026 | 10/1961 | Poland . |
| 748024 | 4/1956 | United Kingdom . |
| 2137612 | 10/1984 | United Kingdom . |
| 7800005 | 12/1978 | World Int. Prop. O. . |
| 8303920 | 11/1983 | World Int. Prop. O. . |
| 8402643 | 7/1984 | World Int. Prop. O. . |
| 8502772 | 7/1985 | World Int. Prop. O. . |
| 8504330 | 10/1985 | World Int. Prop. O. . |

OTHER PUBLICATIONS

Saini, S. et al., Radiology, (1987), 162, 217.

(List continued on next page.)

Primary Examiner—C. Fred Rosenbaum
Assistant Examiner—Sharon Rose
Attorney, Agent, or Firm—Pennie and Edmonds

[57] ABSTRACT

This invention relates to materials exhibiting certain magnetic and biological properties which make them uniquely suitable for use as magnetic resonance imaging (MRI) agents to enhance MR images of animal organs and tissues. More particularly, the invention relates to the in vivo use of biologically degradable and metabolizable superparamagnetic metal oxides as MR contrast agents. Depending on their preparation, these metal oxides are in the form of superparamagnetic particle dispersoids or superparamagnetic fluids where the suspending medium is a physiologically-acceptable carrier, and may be uncoated or surrounded by a polymeric coating to which biological molecules can be attached. These materials are administered to animals, including humans, by a variety of routes and the metal oxides therein collect in specific target organs to be imaged; in the case of coated particles, the biological molecules can be chosen to target specific organs or tissues. The biodistribution of the metal oxides in target organs or tissues results in a more detailed image of such organs or tissues because the metal oxides, due to their superparamagnetic properties, exert profound effects on the hydrogen nuclei responsible for the MR image. In addition, the dispersoids and fluids are quite stable and, in the case of the fluids, can even be subjected to autoclaving without impairing their utility. Furthermore, the materials are biodegradable and, in the case of iron oxide compounds, can eventually be incorporated into the subject's hemoglobin, making them useful in treating anemia. Thus, the materials are well-suited for in vivo use.

4 Claims, 7 Drawing Sheets

U.S. PATENT DOCUMENTS

| | | |
|---|---|---|
| 2,820,740 | 1/1958 | London et al. |
| 2,862,920 | 12/1958 | Berger et al. |
| 3,093,545 | 6/1963 | Westfal et al. |
| 3,100,202 | 8/1963 | Muller et al. |
| 3,228,881 | 1/1966 | Thomas |
| 3,234,209 | 2/1966 | Floramo |
| 3,275,514 | 9/1966 | Saltman |
| 3,480,555 | 11/1969 | Jackson et al. |
| 3,531,413 | 9/1970 | Rosensweig |
| 3,700,595 | 10/1972 | Kaiser |
| 3,843,540 | 10/1974 | Reimers et al. |
| 3,928,581 | 12/1975 | Dahlberg et al. |
| 4,001,288 | 1/1977 | Gable et al. |
| 4,019,994 | 4/1977 | Kelley |
| 4,025,448 | 5/1977 | Sudol |
| 4,101,435 | 7/1978 | Hasegawa et al. |
| 4,230,685 | 10/1980 | Senyei et al. |
| 4,247,406 | 1/1981 | Widder et al. |
| 4,331,654 | 5/1982 | Morris |
| 4,345,588 | 2/1982 | Widder et al. |
| 4,346,709 | 8/1982 | Schmitt ............... 604/897.1 |
| 4,356,098 | 10/1982 | Chagnon |
| 4,357,259 | 11/1982 | Senyei et al. |
| 4,452,773 | 6/1984 | Molday |
| 4,501,726 | 2/1985 | Schroder et al. |
| 4,554,088 | 11/1985 | Whitehead |
| 4,615,879 | 10/1986 | Runge et al. |
| 4,637,929 | 1/1987 | Quay ............................ 424/9 |
| 4,647,447 | 3/1987 | Gries et al. |
| 4,656,026 | 4/1987 | Coffman et al. |
| 4,675,173 | 6/1987 | Widder ........................ 128/654 |
| 4,687,659 | 8/1987 | Quay ........................... 128/654 |
| 4,731,239 | 3/1988 | Gordon |
| 4,749,560 | 6/1988 | Elgavish ...................... 128/654 |
| 4,749,695 | 6/1988 | Schwengers |
| 4,758,422 | 7/1988 | Quay ........................... 128/654 |
| 4,770,183 | 9/1988 | Groman et al. ............. 128/654 |
| 4,795,698 | 1/1989 | Owen |

OTHER PUBLICATIONS

Widder, D. J.: et al., *Amer. J. Roentgenol,* (1987), 148, 399.
Olsson, M. B. E. et al., *Magnetic Resonance Imaging,* (1986), 4, 142.
Ohgushi, M. et al., *J. Magnetic Resonance,* (1978), 29, 599.
Renshaw, P. F. et al., *Mag. Resonan. in Medicine,* (1986), 3, 217.
Lauffer, R. B. et al., *J. Comput. Assist. Tomography,* (1985), 9(3), 431.
Dias, M. H. M.; Lauterbur, P. C., *Mag. Reson. in Medicine, (1986),* 3, 328.
Brasch, R. C., *Radiology,* (1983), 147, 781.
Wolf, G. L., *Magnetic Resonance Annual,* 1985, p. 231.
Weinmann, H. J. et al., *Amer. J. Roentgenol.,* (1984), 142.
Runge, P. M. et al., *Radiology,* (1983), 147, 789.
Greif, W. L., *Radiology,* (1985), 157, 461.
Wesbey, G. E. et al., *Radiology,* (1983), 149, 175.
Kaiser, R.; Miskolczy, G. J., *J. Appl. Phys.,* (1970), 41, 1064.
Elmore, W. C., *Physical Rev.,* (1938), 54, 309.
Weiss, R. D. et al., *J. Appl. Phys.,* (1985), 57, 4274.
Welo, L. A.; Baudisch, O., *Chem. Rev.,* (1934), 15, 45.
Kaiser, R.; Miskolszy, G., 1970 INTERMAG Conference, Washington, D.C., Apr. 21-24.
Elmore, W. C., *Physical Rev.,* (1938), 54, 1092.
Koch, A. J.; Becker, J. J., *J. Appl. Phys.,* (1968), 39, 1261.
Elmore, W. C., *Physical Rev.,* (1937), 51, 982.
McKeehan, L. W.; Elmore, W. C., *Physical Rev.,* (1934), 46, 226.
Bancroft, W. D., *Appl. Coll. Chem., Gen. Theory,* 3rd Ed., (1932).
Travis, P. M., Mechanochemistry and the Colloid Mill Including the Practical Applications of Fine Dispersion (1928), Book Dept., Chem. Cat. Co., Inc.
Driscoll, C. F. et al., *Microvas, Res.,* (1984), 27, 353.
Senyei, A. E. et al., *Metho. Enzymol,* (1985), 112, 56.
Shliomis, M. I., *Sov. Phys.-Usp.,* (1974), 17, 153.
Cox, J. S. G. et al., *J. Pharm. Pharmac.,* (1972), 24, 513.
Marshall, P. R.; Rutherford, D., *J. Coll. Interface Sci.,* (1971), 37, 390.
Richetts, C. R. et al., *Nature,* (1965), 5007, 237.
Muller, A., *Arzheim, Forsch.,* (1967), 17, 921.
Bersin, T., *Pharm. Acta Helv.,* (1964), 39, 657.
Widder, K. J. et al., *Eur. J. Can. Clin. Oncol.,* (1983), 19, 135.
Widder, K. et al., *J. Pharm. Sci.,* (1979), 68, 79.
Alfidi, R. J. et al., *Radiology,* (1982), 143, 175-181.
Mann, S. et al., *J.S.C. Chem. Comm.,* (1979), 1067.
Ashley, D. L. and Goldstein, J. H., *Biochem. Biophys. Res. Commun.,* (1980), 97(1), 114-120.
Majumdar, S. et al., *Magnetic Resonance Imaging,* (1988), 6, 611-615.

(List continued on next page.)

OTHER PUBLICATIONS

Schmiedel, U. et al., *Invest. Radiol.*, (1987), 22, 713–721.
Schmiedel, U. et al., *Radiology*, (1987), 162, 205–210.
Schmiedel, U. et al., *Amer. J. Roentgen.*, (1986), 147, 1263–70.
Runge, V. M. et al., *Radiology*, (1984), 153, 171–176.
Huberty, J. et al., *Magnetic Reson. in Med.*, (1984), V1(N2), 175–176.
Yen et al., U.S. Pat. No. 4,157,323, 1979.
Kennedy and Chaplin, U.S. Pat. No. 4,070,246, 1978.
Wikswo et al., U.S. Pat. No. 3,980,076, 1976.
Abe et al., U.S. Pat. No. 3,932,805, 1976.
Frei et al., U.S. Pat. No. 3,870,645, 1975.
Brown, International Application No. WO 86/0112, 1986.
Frei et al., *J. App. Phys.*, 1986, 39(2), 999–1001.
Frei et al., *IEEE Transactions on Magnetics*, 1970, 6(2), 348–349.
Wesbey et al., *Physiological Chemistry and Physics and Medical NMR*, 1984, 16, 145–155.
Lauterbur et al., *Frontiers of Biological Energetics, Vol. I: Electrons to Tissues*, Dutton, P. L. et al., (Eds.), Academic Press, New York, NY, (1978), pp. 752–759.
Griffeth et al., in *Book of Abstracts, The Society of Magnetic Resonance in Medicine*, 1983, 144–145.
Olsson, M. et al., *Eur. Soc. Nucl. Magn. Reson. Med.*, (1984), Oct. 5 and 6, Geneva, Switzerland, p. 27.
Payne, J. A. et al., *Ibid.*, p. 27.
Persson, B. R. R. et al., *Ibid.*, p. 27.
Gibb, F. R.; Morrow, P. E., *J. Appl. Physiol.*, (1962), 17(3), 429.
Morrow, P. E. et al., *Health Physics*, (1964), 10(8), 543.
Cohen, D. et al., *Science*, (1979), 204, 514.
Weissleder, R. et al., *Am. J. Roentgen.*, (1988), 150, 115.
Weissleder, R. et al., *Am. J. Roentgen.*, (1988), 150, 561.
Weissleder, R. et al., *Am. J. Roentgen.*, (1987), 149, 1161.
Weissleder, R. et al., *Radiol.*, (1988), 166, 423.
Tsang, Y.-M. et al., *Radiol.*, (1988), 167, 21.
Hemmingsson, A. et al., *Acta Radiologica*, (1987), 28(6), 703.
Ogan, M. D. et al., *Invest. Radiol.*, (1987), 22, 665.
Englestad, B. L., *Diag. Imag.*, (1987), 144, March.
Bacon, B. R. et al., *J. Lab. Clin. Med.*, (1987), 110, 164.
Saini, S. et al., *Radiol.*, (1987), 162, 211.
Hahn, P. F. et al., *Radiol.*, (1987), 164, 37.
Kent, T. A. et al., *Soc. of Magn. Res. in Med.*, (abstract), (1987), 5, (August).
Molday, R. S.; Mackenzie, D., *J. Immunol. Methods*, (1982), 52, 353.
Gehr, P. et al., *Nature*, (1983), 302, 336.

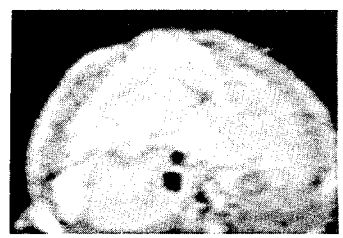 
FIG. 2A  FIG. 2B
 
FIG. 2C  FIG. 2D
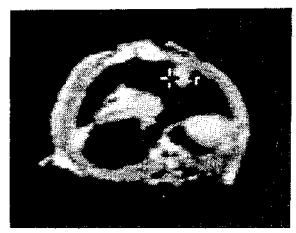
FIG. 2E 5 mM                    10 mM 100mM   50mM   25mM   15mM   10mM   5mM

BIODEGRADABLE SUPERPARAMAGNETIC METAL OXIDES AS CONTRAST AGENTS FOR MR IMAGING

CROSS REFERENCE TO RELATED APPLICATION

This application is a continuation of applicants' prior co-pending U.S. application Ser. No. 067,586 filed June 26, 1987, now U.S. Pat. No. 4,827,945, which in turn, is a continuation-in-part of the applicants' prior co-pending U.S. application Ser. No. 882,044 filed July 3, 1986, now U.S. Pat. No. 4,770,183, the disclosures of which are incorporated herein by reference.

INTRODUCTION

This invention relates to materials exhibiting certain magnetic and biological properties which make them uniquely suitable for use as magnetic resonance imaging (MRI) agents to enhance MR images of animal organs and tissues. More particularly, the invention relates to the in vivo use of biologically degradable and metabolizable superparamagnetic metal oxides as MR contrast agents. Depending on their preparation, these metal oxides are in the form of superparamagnetic particle dispersoids or superparamagnetic fluids where the suspending medium is a physiologically-acceptable carrier. These dispersoids and fluids are administered to animals, including humans, by a variety of routes and the metal oxides therein collect in specific target organs to be imaged. The biodistribution of the metal oxides in target organs or tissues results in a more detailed image of such organs or tissues because the metal oxides due to their superparamagnetic properties, exert profound effects on the hydrogen nuclei responsible for the MR image. In addition, the dispersoids and fluids are quite stable and, in the case of the fluids, can even be subjected to autoclaving without impairing their utility. Thus, the materials are well-suited for in vivo use.

The combination of superparamagnetism and biodegradability makes the materials described herein particularly advantageous for use as MR contrast agents. Superparamagnetism, which results in profound capabilities to alter MR images, makes it possible to use these materials in concentrations lower than those required for MRI with other types of magnetic materials. Biodegradability results in optimum retention times within the organs and tissues to be imaged, i.e., the materials remain within the organ or tissue sufficiently long to permit an image to be obtained, yet are eventually cleared from or metabolized within the organ or tissue. Remarkably, when iron-based agents are administered, the iron thereon is eventually metabolized and incorporated into the subject's hemoglobin.

These materials can, therefore, be used for a variety of clinical diagnostic purposes including, but not limited to, detection of cancerous lesions in liver and other reticuloendothelial tissue, detection of cancerous or other lesions in the intestine, detection of liver diseases, such as cirrhosis and hepatitis, and assessment of liver regeneration. Those that are iron-based are also clinically useful as antianemia agents.

2 BACKGROUND OF THE INVENTION

2.1 In Vivo NMR Imaging: General Considerations

Nuclear magnetic resonance (NMR) is now widely used for obtaining spatial images of human subjects for clinical diagnosis. Clinical usage of NMR imaging, also called magnetic resonance imaging or, simply, MRI, for diagnostic purposes has been reviewed [see e.g., Pykett, et al., Nuclear Magnetic Resonance, pgs. 157–167 (April, 1982) and T. F. Budinger, et al., Science, pgs. 288–298, (October, 1984)]. Several advantages of using such a procedure over currently used diagnostic methods, e.g., x-ray computer-aided tomography (CT), are generally recognized. For instance, the magnetic fields utilized in a clinical NMR scan are not considered to possess any deleterious effects to human health (see Budinger, supra., at 296). Additionally, while x-ray CT images are formed from the observation of a single parameter, x-ray attenuation, MR images are a composite of the effects of a number of parameters which are analyzed and combined by computer. Choice of the appropriate instrument parameters such as radio frequency (Rf), pulsing and timing can be utilized to enhance (or, conversely, attenuate) the signals of any of the image-producing parameters thereby improving the image quality and providing better anatomical and functional information. Finally, the use of such imaging has, in some cases, proven to be a valuable diagnostic tool as normal and diseased tissue, by virtue of their possessing different parameter values, can be differentiated in the image.

In MRI, the image of an organ or tissue is obtained by placing a subject in a strong external magnetic field and observing the effect of this field on the magnetic properties of the protons (hydrogen nuclei) contained in and surrounding the organ or tissue. The proton relaxation times, termed $T_1$ and $T_2$, are of primary importance. $T_1$ (also called the spin-lattice or longitudinal relaxation time) and $T_2$ (also called the spin-spin or transverse relaxation time) depend on the chemical and physical environment of organ or tissue protons and are measured using the Rf pulsing technique; this information is analyzed as a function of distance by computer which then uses it to generate an image.

The image produced, however, often lacks definition and clarity due to the similarity of the signal from other tissues. To generate an image with good definition, $T_1$ and/or $T_2$ of the tissue to be imaged must be distinct from that of the background tissue. In some cases, the magnitude of these differences is small, limiting diagnostic effectiveness. Thus, there exists a real need for methods which increase or magnify these differences. One approach is the use of contrast agents.

2.2. MRI Contrast Agents

As any material suitable for use as a contrast agent must affect the magnetic properties of the surrounding tissue, MRI contrast agents can be categorized by their magnetic properties.

Paramagnetic materials have been used as MRI contrast agents because of their long recognized ability to decrease $T_1$ [Weinmann et al., Am. J. Rad. 142, 619 (1984), Greif et al. Radiology 157, 461 (1985), Runge, et al. Radiology 147, 789 (1983), Brasch, Radiology 147, 781 (1983)]. Paramagnetic materials are characterized by a weak, positive magnetic susceptibility and by their inability to remain magnetic in the absence of an applied magnetic filed.

Paramagnetic MRI contrast agents are usually transition metal ions of iron, manganese or gadolinium. They may be bound with chelators to reduce the toxicity of the metal ion (see Weinman reference above). Paramagnetic materials for use as MRI contrast agents are the subject of a number of patents and patent applications. (See EPA No. 0 160 552; UK Application No. 2 137 612A; EPA No. 0 184 899; EPA No. 0 186 947; U.S. Pat. No. 4,615,879; PCT No. WO 85/05554; and EPA No. 0 210 043).

Ferromagnetic materials have also been used as contrast agents because of their ability to decrease $T_2$ Medonca-Dias and Lauterbur, Magn. Res. Med. 3, 328, (1986); Olsson et al., Mag Res. Imaging 4, 437 (1986); Renshaw et al. Mag Res. Imaging 4, 351 (1986) and 3, 217 (1986)]. Ferromagnetic materials have high, positive magnetic susceptibilities and maintain their magnetism in the absence of an applied field. Ferromagnetic materials for use as MRI contrast agents are the subject of recent patent applications [PCT No. WO 86/01112; PCT No. WO 85/043301].

A third class of magnetic materials termed superparamagnetic materials have been used as contrast agents [Saini et al Radiology, 167, 211 (1987); Hahn et al., Soc. Mag Res. Med. 4(22) 1537 (1986)]. Like paramagnetic materials, superparamagnetic materials are characterized by an inability to remain magnetic in the absence of an applied magnetic field. Superparamagnetic materials can have magnetic susceptibilities nearly as high as ferromagnetic materials and far higher than paramagnetic materials [Bean and Livingston J. Appl. Phys. suppl to vol. 30, 1205, (1959)].

Ferromagnetism and superparamagnetism are properties of lattices rather than ions or gases. Iron oxides such as magnetite and gamma ferric oxide exhibit ferromagnetism or superparamagnetism depending on the size of the crystals comprising the material, with larger crystals being ferromagnetic [G. Bate in *Ferromagnetic Materials*. vol. 2, Wohlfarth (ed.) p.439].

As generally used, superparamagnetic and ferromagnetic materials alter the MR image by decreasing $T_2$ resulting in image darkening. When injected, crystals of these magnetic materials accumulate in the targeted organs or tissues and darken the organs or tissues where they have accumulated. Abnormal volumes of liver, such as tumors, are deficient in their ability to take up the magnetic materials and appear lighter against normal background tissue than they would without contrast agent.

2.3 Superparamagnetic Materials

As stated supra, superparamagnetic materials possess some characteristics of paramagnetic and some characteristics of ferromagnetic materials. Like paramagnetic materials, superparamagnetic materials rapidly lose their magnetic properties in the absence of an applied magnetic field; they also possess the high magnetic susceptibility and crystalline structure found in ferromagnetic materials. Iron oxides such as magnetite or gamma ferric oxide exhibit superparamagnetism when the crystal diameter falls significantly below that of purely ferromagnetic materials.

For cubic magnetite ($Fe_3O_4$) this cut-off is a crystal diameter of about 300 angstroms [Dunlop, J. Geophys. Rev. 78 1780 (1972)]. A similar cut-off applies for gamma ferric oxide [Bare in *Ferromagnetic Materials*, vol. 2, Wohfarth (ed.) (1980) p. 439]. Since iron oxide crystals are generally not of a single uniform size, the average size of purely ferromagnetic iron oxides is substantially larger than the cut-off of 300 angstroms (0.03 microns). For example, when gamma ferric oxide is used as a ferromagnetic material in magnetic recording, (e.g., Pfizer Corp. Pf 2228), particles v 30 are needle-like and about 0.35 microns long and 0.06 microns thick. Other ferromagnetic particles for data recording are between 0.1 and 10 microns in length [Jorgensen, *The Complete Handbook of Magnetic Recording*, p. 35 (1980)]. For a given type of crystal, preparations of purely ferromagnetic particles have average dimensions many times larger than preparations of superparamagnetic particles.

The theoretical basis of superparamagnetism has been described in detail by Bean and Livington [*J. Applied Physics*, Supplement to volume 30, 1205 (1959)]. Fundamental to the theory of superparamagnetic materials is the destabilizing effect of temperature on their magnetism. Thermal energy prevents the alignment of the magnetic moments present in superparamagnetic materials. After the removal of an applied magnetic field, the magnetic moments of superparamagnetic materials still exist, but are in rapid motion, causing a randomly oriented or disordered magnetic moment and, thus, no net magnetic field. At the temperatures of biological systems and in the applied magnetic fields of MR imagers, superparamagnetic materials are less magnetic than their ferromagnetic counterparts. For example, Berkowitz et al. [(J. App. Phys. 39, 1261 (1968)] have noted decreased magnetism of small superparamagnetic iron oxides at elevated temperatures. This may in part explain why workers in the field of MR imaging have looked to ferromagnetic materials as contrast agents on the theory that the more magnetic a material is per gram, the more effective that material should be in depressing $T_2$ [Drain, Proc. Phys. Soc. 80, 1380 (1962); Medonca-Dias and Lauterur, Mag. Res. Med. 3, 328 (1986)].

2.4. Water-Based Superparamagnetic Solutions

It has been recognized for some time that superparamagnetic particles can be fashioned into magnetic fluids termed ferrofluids [see Kaiser and Miskolczy, J. Appl. Phys. 41 3 1064 (1970)]. A ferrofluid is a solution of very fine magnetic particles kept from settling by Brownian motion. To prevent particle agglomeration through Van der Waals attractive forces, the particles are coated in some fashion. When a magnetic field is applied, the magnetic force is transmitted to the entire volume of liquid and the ferrofluid responds as a fluid, i.e. the magnetic particles do not separate from solvent.

Another approach to synthesizing water-based magnetic compounds is disclosed by Gable et al (U.S. Pat. No. 4,001,288). Here, the patent discloses that magnetite can be reacted with a hydroxycarboxylic acid to form a water soluble complex that exhibits ferromagnetic behavior both in the solid form and in solution.

2.4.1. Problems Manipulating Aqueous Solutions of Superparamagnetic Materials Approaches to the synthesis of aqueous fluids of superparamagnetic iron oxides often involve surrounding iron oxide crystals with polymer or surfactants in an effort to block the attractive forces between the crystals that promote aggregation. In many cases however, the polymer does not completely coat the oxide and the resultant material maintains much of the sensitivity to clumping or aggregation characteristic of the uncoated iron oxide. The tendency to clump, and other peculiar properties of iron oxide solutions, hamper the manipulations of these solutions needed in pharmaceutical manufacture.

The manufacture of a magnetic pharmaceutical solution such as an MRI contrast agent requires an extremely stable solution so certain manipulations, common in pharmaceutical manufacture, can be carried out. Solution stability is defined as the retention of the size of the magnetic material in solution; in an unstable solution the material will clump or aggregate. Such changes in the size of magnetic material alter its biodistribution after injection, an intolerable situation for an MRI contrast agent. A high degree of stability is required to perform common operations associated with pharmaceutical manufacture such as dialysis, concentration, filtration, centrifugation, storage of concentrates prior to bottling, and long term storage after bottling. Particular problems are posed by the need to sterilize aqueous solutions of metal oxide, e.g. iron oxide, for pharmaceutical use.

Additionally, concentrated solutions of aqueous superparamagnetic materials cannot be sterilized by filtration even when the solution is comprised of materials smaller than the pore of the filter. This phenomena is related to the concentration of the solution, for dilute solutions can be filter sterilized. Filter-sterilized, dilute material can be reconcentrated and dispensed into sterile bottles, but such operations offer many chances to recontaminate the product. Autoclaving solutions of superparamagnetic materials after bottling is preferable, since sterilization is achieved after final bottling, and there is little opportunity for contamination of the final product. Autoclaving involves heating sealed solutions to 121° C. for 30 minutes Such extreme temperatures induce aggregation or clumping of the superparamagnetic oxides, making them unusable as an injectable material.

2.5. Paramagnetic Ferric Oxides

Paramagnetic iron oxides or ferric oxides are currently used in the treatment of anemia under many trade names such as Imferon. When dissolved in aqueous solution, such materials can be represented as FeO:OH and are termed ferric oxyhydroxides. They are paramagnetic and exert small, if any, effects of proton relaxivity. They are stable, undergo the manipulations discussed supra for pharmaceutical manufacture, and are commercially available as drugs used in the treatment of anemia.

3. NOMENCLATURE

The term "biodegradable" in reference to the materials of this invention is defined as being metabolized and/or excreted by the subject within 30 days or less; for superparamagnetic iron oxides, the term is further defined as being incorporated into the hemoglobin of a subject within 30 days or less after administration.

The term "blocking agent" is defined as any material which when administered parenternally to a subject, will competitively bind to the receptors of the cells of the reticuloendothelial system which recognize and bind MRI contrast agents.

The term "superparamagnetic fluid" defines any metal oxide fluid produced by the methods described in section 6.3 herein, which has the characteristics described in section 6.4 herein.

4. Summary of the Invention

It is an object of this invention to provide an in vivo MR imaging technique for diagnostic purposes which will produce a clear, well-defined image of a target organ or tissue. Specifically, it is an object of this invention to provide an imaging method using MR contrast agents which are easily administered, exert a significant effect on the image produced and which distribute in vivo to specific organs or tissues. These contrast agents are stable in vivo, can be easily processed for in vivo use, and overcome problems of toxicity and excessively long retention in the subject (i.e. are biodegradable). It is further an object of this invention to provide a means whereby these contrasts agents can be directed, in vivo, to a specific target organ or tissue.

This invention provides a novel MR imaging method using biodegradable superparamagnetic metal oxides as contrast agents which fulfill the foregoing objectives. Such materials, it has been discovered, combine an optimal balance of features and are particularly well-suited for use as MR contrast agents. Remarkably, it has been found that these superparamagnetic materials exert a greater effect on $T_2$ than ferromagnetic or paramagnetic materials, thereby producing a well-resolved, negative contrast image of an in vivo target organ or tissue. It has also been surprisingly found that the materials used in the methods of this invention exhibit highly desirable in vivo retention times, i.e., they remain intact for a sufficient time to permit the image to be taken, yet are ultimately biodegradable. Remarkably, once degraded, iron-based materials serve as a source of nutritional iron. Additionally, they are sufficiently small to permit free circulation through the subject's vascular system and rapid absorption by the organ/tissue being imaged, allowing for maximum latitude in the choice of administration routes and ultimate targets.

In one embodiment, the materials used as MR imaging agents comprise superparamagnetic metal oxide particles which comprise superparamagnetic crystalline cores. Each core is composed of magnetically active metal oxide crystals which range from about 10 to about 500 angstroms in diameter. The cores may be uncoated or, alternatively, coated or associated with a polysaccharide, a protein, a polypeptide or any composite thereof. By way of illustration, the polysaccharide coating may comprise dextran of varying molecular weights and the protein coating may comprise bovine or human serum albumin. With coatings, the overall particle diameter ranges from about 10 upward to about 5,000 angstroms. In the case of coated particles, the coatings can serve as a base to which various biological molecules can be attached. The biological molecules can be used to direct the particles to the desired target and are preferentially recognized and bound by the target organ or tissue. Such molecules include proteins, polysaccharides, hormones, antibodies, etc.

Preferred superparamagnetic particles comprise iron oxides with crystal sizes ranging from about 50 to about 500 angstroms. These iron oxide particles have surface areas greater than 75 $m^2$/gram. In aqueous solution, these iron oxide particles have a size range between about 50 and about 5,000 angstroms, including coatings, if any. The superparamagnetic iron oxides have magnetic saturations between about 5 and about 90 electromagnetic units (EMU) per gram of oxide at room temperature (approximately 25° C.) and possess a magnetic squareness of less than 0.10, i.e., lose greater than 90% of their magnetism when an applied magnetic field is removed.

Superparamagnetic particles with these general dimensions overcome problems associated with the use of ferromagnetic and paramagnetic materials as MR contrast agents. Specifically, superparamagnetic particles, because they are smaller than ferromagnetic particles, are more able to avoid uptake by the subject's reticuloendothelial cells and may be more effectively targeted to other organ and tissue sites within the body. Also, because the superparamagnetic particles are smaller than ferromagnetic particles, they have higher surface area per unit mass and are more easily and rapidly digested by chemical or metabolic processes. However, the superparamagnetic particles used herein, because they are larger than paramagnetic ions, are not so rapidly metabolized in the target organ or tissue as to prevent convenient imaging.

Uncoated or coated particles may be suspended in an appropriate medium (e.g., saline) to form a particle dispersoid that has the properties of a solution. The particles do not settle upon standing and do not scatter visible light (i.e., the solution appears translucent). Solvent can be added (decreasing) or removed (increasing) particle concentration.

This dispersoid of particles may be administered to the subject being studied. Depending on the route of administration, the particles are distributed to various target organs, where absorption occurs. For example, when the superparamagnetic particles are administered intravascularly (e.g., intravenously or intra-arterially), they are selectively distributed to reticuloendothelial organs, including liver, spleen, lymph nodes and bone marrow and, to a lesser extent, lung. However, when the superparamagnetic particles are administered via the gastrointestinal tract, e.g., orally, by intubation or by enema, they can be used as imaging agents for the organs and tissues of the gastrointestinal tract.

The use of sub-micron sized particles is particularly important when the route of administration is intravascular, as such particles can freely circulate in the subject's vascular system, since they are small enough to pass through the capillary network. Thus, such contrast agents can be carried to targeted organs or tissue after being intravascularly administered with a minimum of trouble or delay.

In one embodiment, a dextran-coated iron oxide particle dispersoid is injected into a subject's bloodstream and the particles localize in the liver. The particles are absorbed by the reticuloendothelial cells of the liver by phagocytic uptake; a particular benefit of this mode of uptake is that phagocytized iron is metabolized and cleared from the liver much more slowly (but not so slowly as to lead to undesirably long retention times) than prior art paramagnetic ions. Additionally, the dextran-coated particles can be preferentially absorbed by healthy cells, with less uptake into cancerous (tumor) cells. This preferential uptake enhances the contrast between healthy and cancerous tissue and allows for better definition of the tumor location on the image.

In another embodiment of this invention, the materials comprise stable, biodegradable superparamagnetic metal oxides, preferably ferric oxides, in the form of superparamagnetic fluids. These superparamagnetic fluids exhibit some of the magnetic properties of superparamagnetic ferrofluids (e.g., the metal oxides in them cannot be removed from solution by magnetic manipulation), yet the metal oxides in them can be easily reclaimed from the bulk fluid by physical means (e.g. centrifugation) and, ultimately redispersed in the bulk fluid. When dispersed, the metal oxides will not scatter visible light, indicating the individual metal oxide "particles" are quite small (generally between 50 and 4000 angstroms in diameter.)

The metal oxides of the invention exist in the bulk fluid as ionic crystals, having both ionic and crystalline characteristics. In common with magnetite ($Fe_3O_4$) and gamma ferric oxide (gamma $Fe_2O_3$) they have high magnetic susceptibility. In common with ionic forms of ferric oxide, the so-called ferric oxyhydroxides, they cause retention of anions. The counterion to the crystals can be any one of a number of organic anions.

In a preferred embodiment, the metal oxide is a superparamagnetic ferric oxyhydroxide and the counterion is citrate. The use of citrate counterions also confers a distinct advantage to the fluids as it renders them highly stable. In fact, the citrated fluids can withstand autoclaving greatly facilitating sterile administration.

The metal oxides in the superparamagnetic fluids may also be surrounded by a coating comprising a polysaccharide, a protein, a polypeptide, an organosilane, or any composite thereof. These polymeric coatings serve a dual purpose, helping to stabilize the superparamagnetic fluids as well as serving as a base to which biological molecules can be attached. These biological molecules can be used to direct particles to the desired target and are preferentially recognized and bound by the target organ or tissue. These molecules include proteins, polysaccharides, hormones, antibodies, etc.

The superparamagnetic fluids, whether comprised of coated or uncoated metal oxides, can be administered to a subject by any of the means described supra for the metal oxide dispersoids. Furthermore, in general the fluids are quite stable and can be prepared well in advance of use and stored.

The superparamagnetic fluids, containing both coated and uncoated metal oxides, are produced by a unique three step process from a mixture of $Fe^{2+}$ and $Fe^{3+}$ salts. In addition, this process permits incorporation of other metals similar to iron (such as cobalt (Co) and manganese (Mn) into the fluids by replacing some of the divalent iron salts with divalent salts of these metals. In the process, the salts are precipitated in base to form the corresponding oxides. These oxides are then dispersed and oxidized by sonication of the mixture; the result, remarkably, is a superparamagnetic ferric oxyhydroxide. Insoluble oxides can then be removed by centrifugation and the final fluid is dialyzed against a neutral or alkaline buffer suitable for in vivo use.

In a preferred embodiment, the salt mixture is $FeCl_2$/$FeCl_3$ in a 1:2 ratio and the buffer is 10 mM ammonium citrate at pH 8.2. The result is a superparamagnetic fluid of unusual stability, characterized by its capacity to withstand autoclaving.

Once administered both the metal oxides of the superparamagnetic particle dispersoids and the superparamagnetic fluids collect in the target organ or tissue and exert a profound contrast effect to permit an image to be taken. The superparamagnetic metal oxides act primarily to enhance $T_2$ relaxation, but $T_1$ is also affected (although to a lesser extent).

Another embodiment of this invention presents a method for extending the lifetime of the superparamagnetic metal oxides in the subject's serum. The method comprises administering a dose of paramagnetic metal oxide in the same form as the superparamagnetic imaging agent (i.e. appropriate particle size and, if applicable, the same coating) as a blocking agent prior to the administration of the imaging agent. This blocking agent will compete with the imaging agent for binding to the reticuloendothelial system (RES) receptors. Since the RES is responsible for removing impurities from the blood, the binding of the blocking agent greatly increases the serum lifetime of the imaging agent. Potential applications of this procedure include, but are not limited to, use of MRI to diagnose blood circulation disorders and strokes.

5. BRIEF DESCRIPTION OF THE FIGURES

FIG. 2 is a composite of five in vivo MR images of a cancerous rat liver obtained on a Technicare MR Imager;

Figure 3:
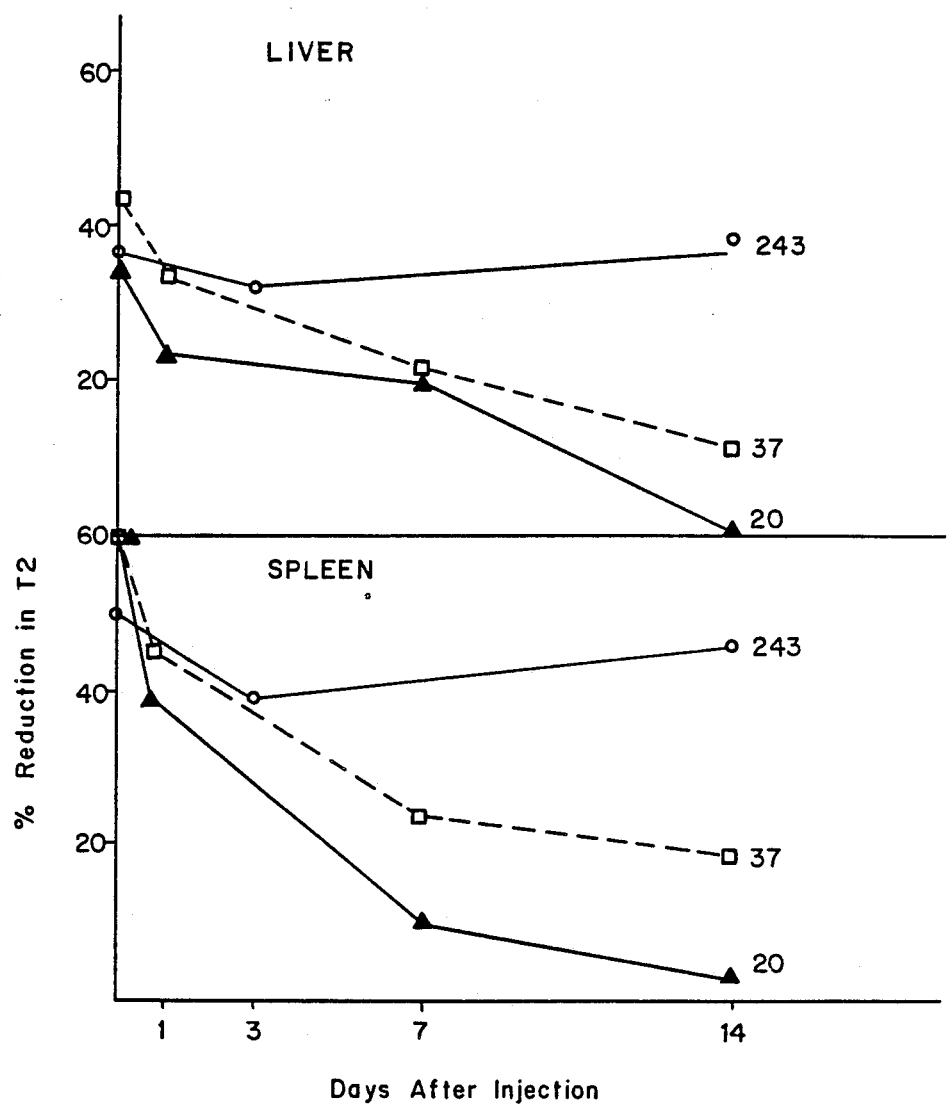
Figure 4:
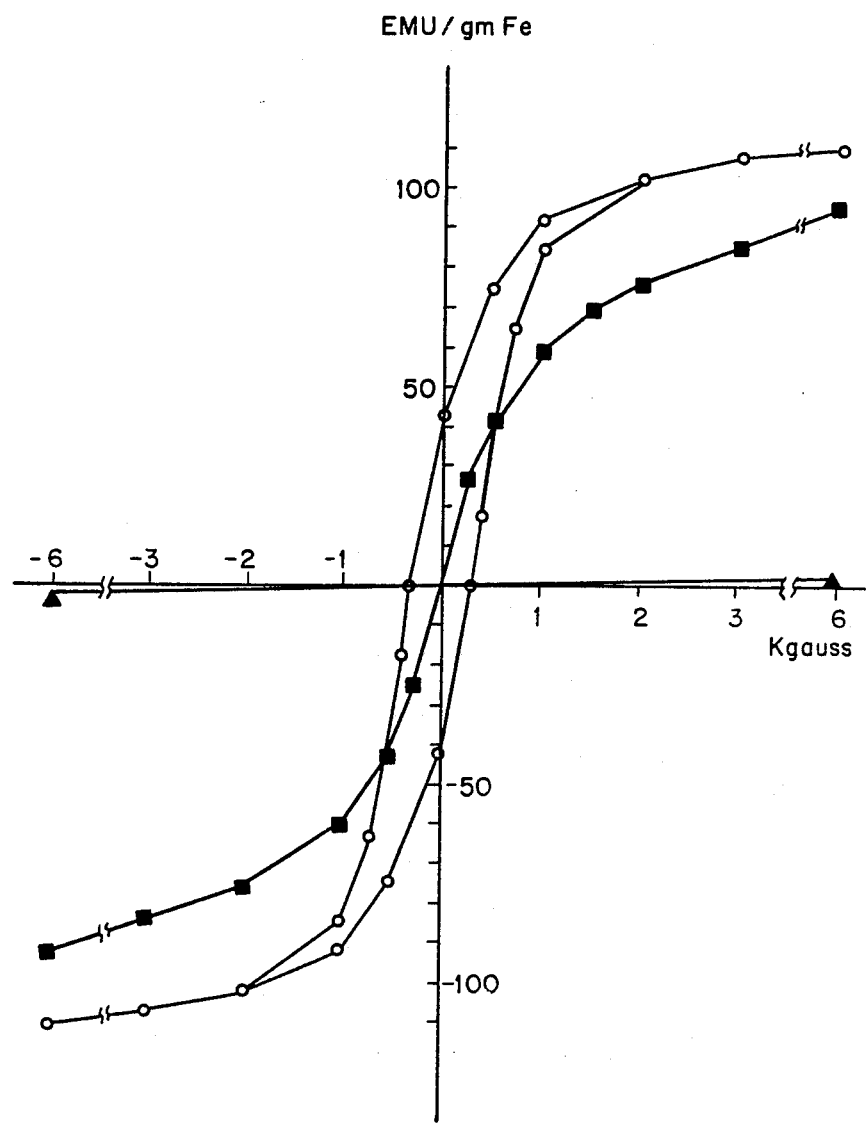
Figure 5A:
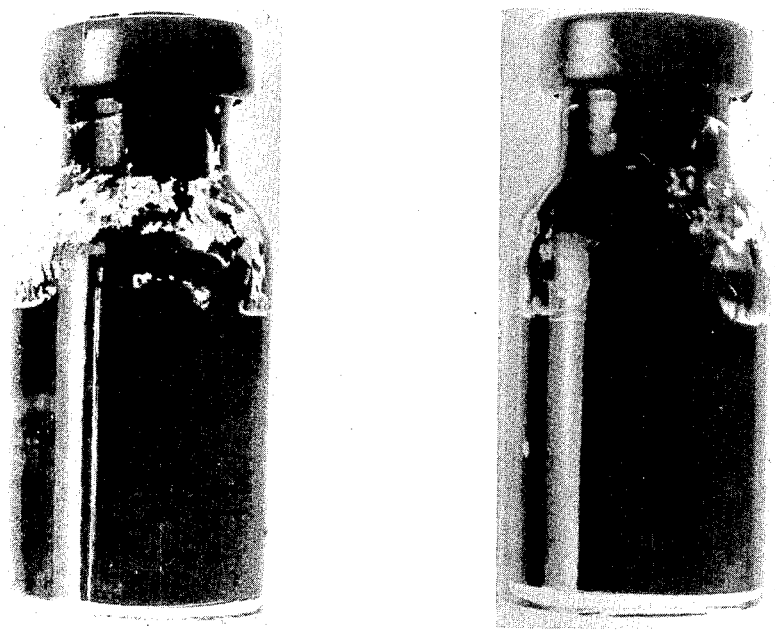
Figure 5B:
Figure 6:
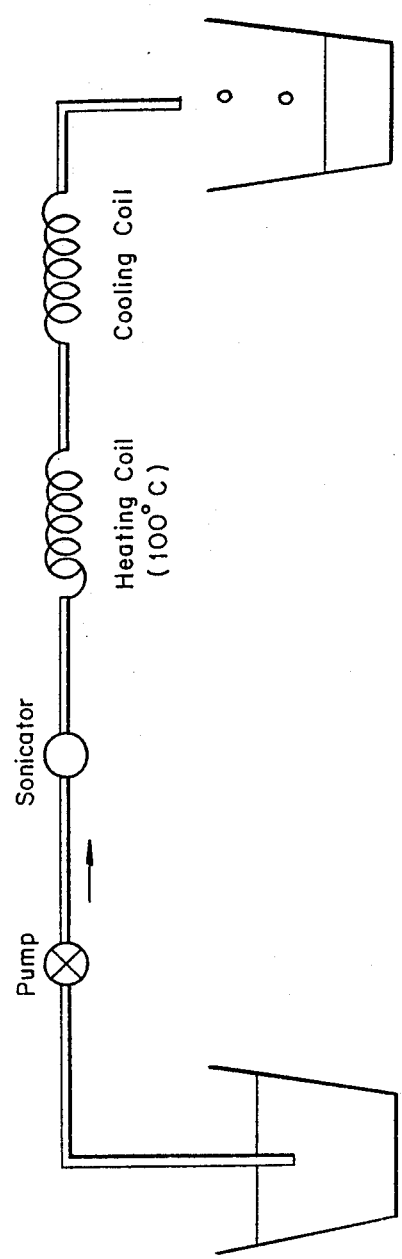

FIGS. 2A and 2B were obtained without the use of contrast agents and were taken at different settings of instrument;

FIGS. 2C and 2D were obtained after the intravenous administration of the dextran-coated particle produced in Example 6.1. at a dosage of 0.5 mg/kg; the tumor can clearly be seen;

FIG. 2E is the image reproduced in FIG. 2C showing the tumor highlighted by crosshairs;

FIG. 3 is a graphical representation of the % $T_2$ reduction in liver and spleen tissue for three different dosages of an uncoated superparamagnetic particle as a function of time after administration;

FIG. 4 presents hysteresis curves for paramagnetic, ferromagnetic and superparamagnetic iron oxides;

FIGS. 5A and 5B shows the effect of autoclaving on superparamagnetic fluids prepared as in Example 7.10 having varying concentrations of citrate;

FIG. 6 presents a schematic diagram of the apparatus used in Example 7.10; and

Figure 7:
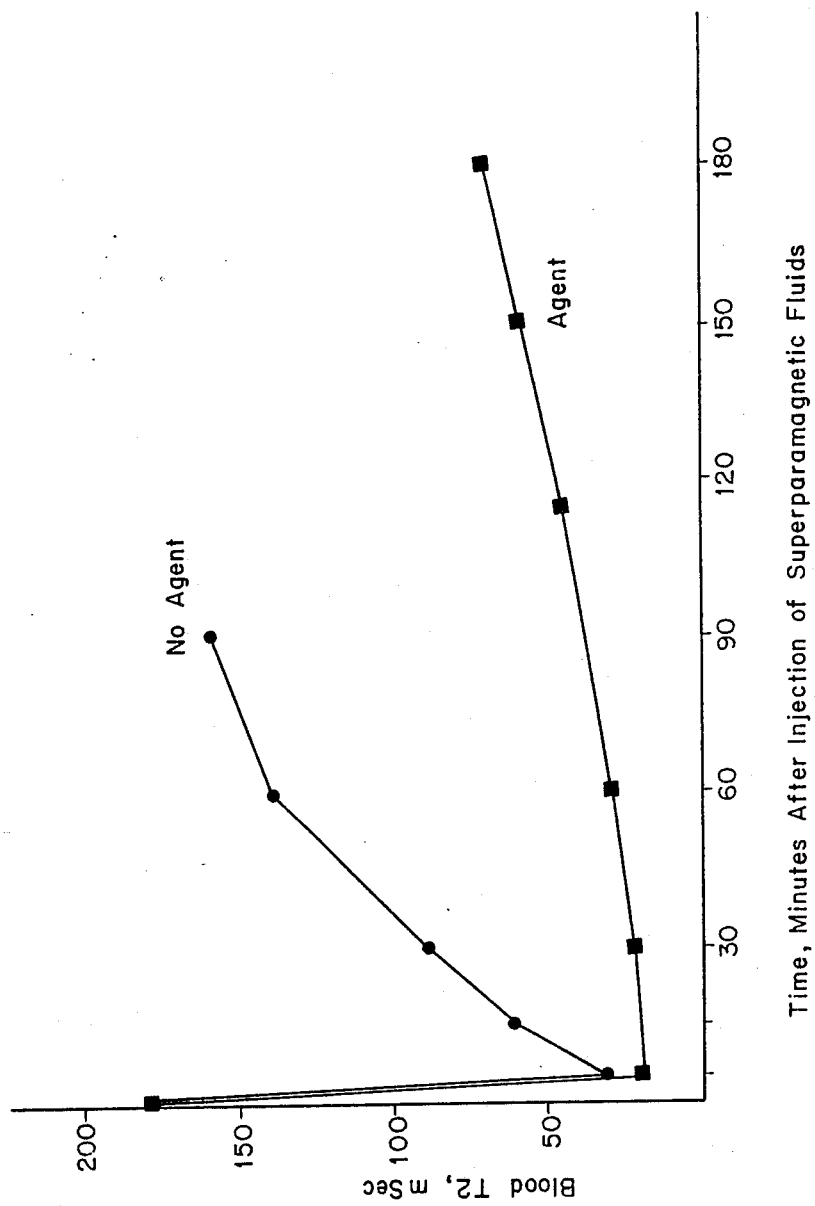

FIG. 7 is a graphical representation of the $T_2$ of rat blood as a function of time after the injection of a dextran-coated superparamagnetic iron oxide particle with and without the use of a blocking agent.

6. DETAILED DESCRIPTION OF THE INVENTION

6.1. Preparation of Coated Superparamagnetic Iron Oxide Particles

The synthesis of superparamagnetic iron oxide particles for use as MRI contrast agents is accomplished by mixing ferrous and ferric salts with base to form a black, magnetic oxide of iron. Crystals result from such precipitations, for when the material is subjected to X-ray diffraction analyses long range order is apparent. A diameter of between about 50 and about 300 angstroms for such crystals has been calculated although crystals may range in diameter from about 10 to about 500 angstroms. The iron oxides have correspondingly high surface areas, greater than about 75 m²/gm.

The presence of ferrous salts prior to base addition insures the formation of a black, crystalline magnetic iron oxide. Without the ferrous ion, paramagnetic ferric oxide gels (noncrystalline materials) result (as described e.g., in U.S. Pat. No. 2,885,393). The presence of divalent iron, so essential to the formation of the superparamagnetic material, can then be removed by exposure of the material to oxidizing conditions. Oxidation of the iron to produce a ferric oxide after formation of the crystal does not alter the usefulness of the material as a contrast agent in MRI or the superparamagnetism.

It is to be understood throughout this detailed description, that the use of superparamagnetic iron oxides as MR contrast agents is but one embodiment of the invention and that superparamagnetic oxides of other magnetic metals, e.g., cobalt or gadolinium, may be substituted for iron oxides.

There are two general strategies for the formation of the coated superparamagnetic iron oxide particles suitable for MRI.

1. Synthesis of iron oxide by precipitation in the presence of polymers like dextran, or polyglutaraldehyde or other material. Such syntheses include those described by London et al., U.S. Pat. No. 2,870,740, Molday, U.S. Pat. No. 4,452,773, Cox et al., *Nature*, 208, 237 (1965) and Rembaum, U.S. Pat. No. 4,267,234; all of which are incorporated herein by reference.

2. Synthesis of the iron oxide by precipitation followed by coating with a polymer like dextran or other material. This type of synthetic route is utilized by Elmore, *Phys. Rev.* 54, 309 (1938) and Ohgushi et al., *J. Mag Res.*, 9, 599 (1978); both of which are incorporated herein by reference.

With proteins and dextrans, synthesis of the oxide in the presence of the polymer seems to effect a tight association between the polymer and the oxide. The synthesis of oxide first, followed by exposure to a protein or dextran yields a coated particle with the coating being held to the particle surface by relatively weak adsorption phenomena. However, if the oxide and adsorbed polymer can be manipulated, stored and injected in the presence of nonadsorbed polymer, the weakness of the association between oxide and polymer is not a problem. For example, when the particles of Section 6.1.3. (uncoated) are diluted 1:1 into a neutral buffer containing 1% w/v human serum albumin (HSA), considerable protein will adsorb to the oxide surface. This approach to the synthesis of an albumin coated magnetic particle is a practical one for an imaging agent. The HSA coated particle (plus HSA in solution) can be injected into a patient and the HSA in solution mixes with HSA in serum. When particles are made by this approach the loosely associated HSA can be removed by treatments such as moderate temperature (50° C.) or high salt (1M NaCl).

The coating methods are general and can be performed with a variety of physiologically acceptable proteins and carbohydrates, particularly those with molecular weights from about 5,000 to about 250,000 daltons. Other polymeric coatings include, but are not limited to, albumin/dextran composites, ficoll, dextrin, starch, glycogen and polyethylene glycol.

6.1.1. Preparation of Polysaccharide-Coated Particles

Polysaccharide-coated superparamagnetic iron oxide particles (about 10 to about 5000 angstroms in diameter) useful as MR contrast agents are prepared by a single-step process according to the procedure of Molday [U.S. Pat. No. 4,452,773] incorporated herein by reference above. In a preferred embodiment, dextranized divalent ($Fe^{2+}$) and trivalent ($Fe^{3+}$) iron salts, e.g. $FeCl_2$ and $FeCl_3$, are precipitated from an aqueous solution containing a mixture of the iron salts and dextran (molecular weight of dextran can vary from 5,000 to 250,000 daltons) by the dropwise addition (to pH=10) of base ammonium hydroxide at 60°-65° C., followed by centrifugation at 1500×g for 15 minutes to remove the oversized particles which are subsequently discarded. The remaining particles are dialyzed against distilled water and can be concentrated by ultrafiltration. Any unbound dextran can be removed by gel filtration chromatography in a chloride/acetate buffer.

The ratio of $Fe^{3+}$ to $Fe^{2+}$ is preferentially maintained at about 2:1, but can be varied from about 0.5:1 to about 4.0:1 without substantial changes in product quality and efficiency as contrast agents.

Likewise, bases other than ammonium hydroxide ($NH_4OH$) can be used, but $NH_4OH$ is preferred because the ammonium ion has a slight dispersing effect on iron oxides which increases the yield.

As mentioned above, various magnetically active metals notably Co, and Mn, may be substituted for Fe without any deleterious effect on the efficiency of the particles as contrast agents. Use of other polysaccharides such as starches, glycogen or dextrins is also contemplated.

6.1.2. Preparation of Protein-Coated Particles

Protein-coated superparamagnetic iron oxide particles are prepared by a single-step process similar to that of Molday [U.S. Pat. No. 4,452,733]. The protein-coated particles can be prepared like the dextran coated wherein the iron salts (e.g., $FeCl_2$ and $FeCl_3$) and the protein are dissolved in water and the coated iron oxide particles are precipitated by the dropwise addition of base ($NH_4OH$) to pH=10. In an alternative embodiment the protein can be dissolved in the base and an aqueous solution of the iron salts can be added dropwise to form a coated particle.

In either method, the oversized particles are subsequently collected by centrifugation at 1500×g and the remaining particles are subjected to dialysis against distilled water followed by ultrafiltration. Any unbound protein can be removed by gel filtration chromatography in a chloride/acetate buffer.

As with the polysaccharide coated particles, both the coating composition and the $Fe^{3+}/Fe^{2+}$ ratio (about 2/1) can be varied from about 0.5:1 to about 4:1 without any deleterious effect on the efficiency of these particles as contrast agents.

As mentioned above, various magnetically active metals notably Co, and Mn, may be substituted for Fe without any deleterious effect on the efficiency of the particles as contrast agents.

6.1. 3. Preparation of Uncoated Particles

Uncoated superparamagnetic iron oxide particles are prepared by mixing an solution of ferric chloride ($FeCl_3$) with ferrous chloride ($FeCl_2$) in HCl and precipitating in 0.7 molar aqueous ammonia. The base precipitation offers a dual advantage in that the base reacts with the iron chlorides to form uncoated superparamagnetic iron oxide particles. The precipitate is then collected by centrifugation or application of a magnetic field followed by decantation of the liquid phase.

The gel is then peptized to form a dispersoid by mixing with either 1 molar aqueous tetramethylammonium hydroxide (to form an alkaline dispersoid) or 2 molar aqueous perchloric acid (to form an acidic dispersoid) followed by centrifugation and redispersion in water. Both of these dispersoids show remarkable stability and, being colloidal in nature, will not possess large solid particles. The counterions, either tetramethlyammonium hydroxide or perchlorate, are charged in basic or acidic media, respectively and, thus, prevent complex coagulation in solution; the particles (complexes of iron oxide/counterions) can be repeatedly precipitated and re-dispersed in solution and will retain this property.

In an alternative embodiment the particles can be collected by the application of an external magnetic field rather than centrifugation. The resultant magnetic cake is then peptized by the appropriate counterion.

The ratio of $Fe^{3+}/Fe^{2+}$ is preferably maintained at about 2/1, but can be varied between about 0.5/1 and about 4/1. Decreasing the ratio will produce larger and increasing the ratio will produce smaller sized particles. Using the 2/1 ratio and 0.7M $NH_4OH$, the average particle size produced is about 1200 angstroms as measured by light scattering.

6.2. Use of the Particles as MR Imaging Agents

The magnetic materials described above can be used as contrast-enhancing agents for in vivo MR imaging. In one embodiment, the particles are dispersed in a suitable injection medium, such as distilled water or normal saline, or any other physiologically acceptable carrier known in the art, to form a dispersoid which is introduced into the subject's vascular system by intravenous injection. The particles are then carried through the vascular system to the target organ where they are taken up.

When intravascularly administered, the particles will be preferentially taken up by organs which ordinarily function to cleanse the blood of impurities, notably the liver, spleen, and lymph nodes, and the other organs which tend to accumulate such impurities, notably bone and neural tissue and to some extent, lung. In each of these organs and tissues, the uptake into the reticuloendothelial cells will occur by phagocytosis, wherein the particles enter the individual cells in membrane-bound vesicles; this permits a longer half-life in the cells, as such membrane-bound particles will not tend to clump or aggregate (aggregates are rapidly metabolized and cleared from the organ/tissue). Other uptake mechanisms are possible, e.g., pinocytosis. Also, it is possible that the other cells of the liver (hepatocytes) may absorb the magnetic particles.

Because cancerous tumor cells can lack the ability of phagocytic uptake, the intravascularly administered particles can serve as valuable tools in the diagnosis of cancer in the above-mentioned organs, as tumors will be immediately distinguishable on any image obtained.

In a another embodiment, the particles are administered as dispersoids in a physiologically acceptable carrier, such as distilled water, into the gastrointestinal tract, which includes the esophagus, stomach, large and small intestine, either orally, by intubation, or by enema, in a suitable medium. The particles are preferentially absorbed by the cells of the tract, especially those of the intestine and, like the intravascularly introduced particles, will exert an effect on $T_2$ of the organ or tissue. In this manner, cancers and other debilitating diseases of the digestive system such as ulcers can be diagnosed and affected areas pinpointed.

Regardless of the route, once administered, the particles distribute to and collect rapidly in the target organs, generally in 30-minutes to an hour.

In the organ, these superparamagnetic particles will alter the magnetic fields produced by the MR imager. These altered fields will exert an effect on the magnetic properties of the hydrogen nuclei (protons) in neighboring molecules; notably affected is the spin-spin relaxation time, $T_2$. This parameter is shortened which can result in image darkening. Thus, the contrast is enhanced between areas which absorb the particles rapidly and those which absorb them slowly or not at all.

The particles are however, ultimately biodegradeable and the iron can be utilized by the body for physiological requirements. The contrast effect will vary with the dose, being longer at higher doses, and also with the organ imaged. Particularly in the liver and spleen (which store iron for physiological use) the effect can be observed for 14 days or more, (see Section 7.6), and, often, as long as 30 days.

The localization in these organs, which store iron for ultimate incorporation into hemoglobin, reveals that the iron oxide particles will ultimately serve as a source of metabolizable iron and, in fact, will be incorporated in the subjects hemoglobin. Thus, these materials can also be useful in the treatment of anemia.

The differences in parameter values are interpreted by computer and used to generate an image of the organ in question. In the cases, as mentioned above, where uptake occurs by phagocytic processes (notably the liver, spleen, lymph nodes, and bone and neural tissue and to some extent, lung) such an image will clearly and distinctly differentiate between cancerous and healthy tissue, allowing for tumor location. In other organs and/or in the diagnosis of other diseases, modifications of the coating of these particles by the attachment of various functional groups will stimulate uptake by the organ or cell of choice. For example antibodies to a particular tumor cell (e.g. lung carcinoma) can be attached to the surface of a coated particle, stimulating uptake by that organ if such a cell is present. In this way, the method can serve a diagnostic tool for many diseases.

6.3. Preparation of Superparamagnetic Fluids

The superparamagnetic fluids useful as imaging agents in this invention are preferably prepared in a three step process which comprises the steps of: formation of a superparamagnetic metal oxide; oxidation and dispersion of this oxide by sonication; and dialysis in buffer. This process yields stable biodegradable superparamagnetic metal oxides that owe their stability primarily to their anion retaining properties. The metal oxides may be uncoated or associated to organic polymeric substances. Each of these steps is discussed separately below.

6.3.1. Formation of Superparamagnetic Metal Oxide

Formation of the superparamagnetic metal oxide is accomplished by mixing the appropriate metal salts with a base. In a preferred embodiment, this is accomplished by mixing an aqueous solution or suspension of divalent and trivalent iron salts ($FeCl_2/FeCl_3$) with a base such as sodium hydroxide (NaOH). In addition, metals similar in structure to iron, such as Co and Mn, can be incorporated into the ultimate superparamagnetic fluid by replacing a portion, preferably ½ or less, of the divalent iron salt with a divalent salt of that metal. The result is when a mixed metal oxide preciptate containing both ferrous and ferric oxides, as well as oxides of the divalent metal.

When iron salts are used the ratio of $Fe^{3+}/Fe^{2+}$ can be varied from ¼ to 4/1 and still produce usable product. Thus, a wide range of salt mixtures can be utilized.

Once the salts are mixed with the base, a superparamagnetic metal oxide precipitate is formed. The use of a high concentration of reactants and an abrupt change in pH favors the formation of small superparamagnetic metal oxides. Such oxides are preferred for use in the subsequent steps of this process.

6.3.2. Dispersion and Oxidation

In the second process step, the superparamagnetic metal oxide prepared in 6.3.1. is dispersed and oxidized further by sonication. The sonication, which can be conducted at ambient or elevated temperatures (up to 100° C.) serves a dual purpose: it serves to disperse any clusters of superparamagnetic particles (which increases the ultimate effects of the material on proton relaxation and, hence, enhances their effectiveness as MR contract agents) and, additionally, it serves to oxidize most, if not all, of ferrous oxide ($Fe^{2+}$) to ferric oxide ($Fe^{3+}$). The resultant material, remarkably, is a soluble superparamagnetic iron oxyhydroxide which forms a superparamagnetic fluid.

The sonication can be accomplished in any commercial apparatus including in a continuous flow sonicator or by a sonic probe. The former is especially useful when large volumes of materials are being handled and, for a continuous process, can be coupled with a heating and cooling apparatus to permit heating of the iron oxide prior to or after sonication (to increase the dispersion and oxidation of the oxides ) and subsequent cooling of the sonicated mixture to facilitate collection.

6.3.3. Dialysis

The final step in the process is the transfer of the solution to an aqueous polycarboxylic buffer suitable for in vivo use. This transfer is accomplished by dialyzing the fluid against the buffer at neutral pH, generally at a pH of 6–9, preferably 6–8.3. These conditions result in a stable superparamagnetic fluid; under acidic conditions (below a pH of about 6) a significant amount of a chelate of the iron begins to form rather than the superparamagnetic iron oxide.

In the process, the fluid from 6.3.2. is centrifuged, to remove larger oxide aggregates, and the supernatant is dialyzed against the buffer. The preferred buffer contains a citrate salt, because of its suitability for in vivo use and its long history as an injectable agent, but in general buffers containing salts of any polycarboxylic acid (such as tartrate, succinate) or maleatic buffers allow for the formation of stable superparamagnetic fluids. The resultant fluids can then be autoclaved and stored until needed.

6.3.4. Preparation of Stable Superparmagnetic Fluids Containing Metal Oxides Associated WITH Organic Polymeric Substances Superparamagnetic fluids containing metal oxides to which organic polymeric substances are associated can be prepared by modifications of the above procedure. Such organic polymers or coatings can be selected from a wide array of polymeric materials including, but not limited to, carbohydrates such as dextran (preferably having a molecular weight between 5,000 and 250,000 daltons), proteins (preferably having a molecular weight between 5,000 and 250,000 daltons) such as bovine or human serum albumin, polypeptides (preferably having molecular weights between 5,000 and 250,000 daltons) such as polylysine and polyglutamates, and polymerizable (preferably to a molecular weight between 5,000 and 250,000 daltons) organosilanes such as N-2-aminoethyl-3-aminopropyltrimethoxysilane. Briefly, attachment or associative procedure the attachment can be accomplished during either the first or the second steps.

When the procedure is accomplished during the first step, the polymeric material is mixed with the salt solution prior to the supermagnetic metal oxide precipitation. The polymeric material is associated to the resultant precipitate, and remains associated during the subsequent steps. Any unbound coating or polymeric agent is removed during dialysis (step 3). In a preferred embodiment, superparamagnetic fluids containing dextranized iron oxides can be formed in this manner.

The procedure can also be performed during the dispersion and oxidation second step by adding the polymeric substance prior to the sonication and subsequently sonicating the mixture to form the corresponding oxyhydroxide. Again, the unbound polymeric agents may be removed by dialysis.

Superparamagnetic fluids containing silanized iron oxides are prepared in a similar manner. Initially, the iron oxides are subjected to sonication to form the oxyhydroxides. The organosilane is then added and the mixture is sonicated to disperse the materials. Finally, the silane is or associated to the surface via a dehydration reaction. The polymerization of the silane may occur before or after the deposition on the oxyhydroxide surface.

In one embodiment, the silanization reaction occurs in two steps First, a trimethoxysilane is placed in the sonicated mixture which condenses to form silane polymers:

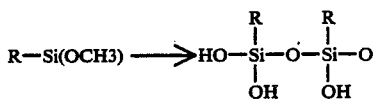

The mixture is then sonicated, after which these polymers associate with the metal oxide, presumably by forming a covalent bond with surface OR groups through dehydration:

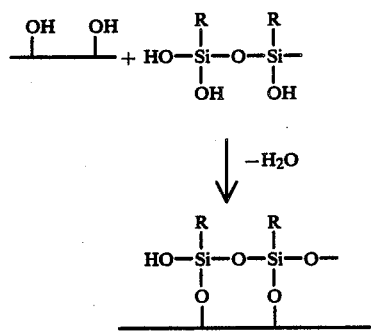

Adsorption of silane polymers to the metal oxide is also possible.

An important aspect of this procedure is the method of dehydration used to effect the adsorptive or covalent binding of the silane polymer to the metal oxide. This association is accomplished by heating the silane polymer and metal oxide in the presence of a wetting agent miscible in both the organic solvent and water. Glycerol, with a boiling point of about 290° C., is a suitable wetting agent. Heating to about 105° C. in the presence of glycerol serves two purposes. It insures the evaporation of water, the organic solvent (which may be e.g., methanol, ethanol, dioxane, acetone or other moderately polar solvents) and any excess silane monomer. Moreover, the presence of glycerol prevents the aggregation or clumping and potential cross linking of particles that is an inherent problem of other silanization techniques known in the art wherein dehydration is brought about by heating to dryness. Thus, few large aggregates are formed. Any large aggregates are removed by centrifugation and the unbound silane is removed by hydrolysis.

6.3.5. Advantages of the Superparamagnetic Fluid Preparation Process

The process used to prepare the superparamagnetic fluids of this invention is uniquely suited for preparing magnetic fluids suitable for in vivo use. Specifically, the following advantages are noted:

1. At no time is the material dried, nor is it precipitated after the intial formation of the superparamagnetic oxides. Such operations bring particles into close proximity with each other resulting in clustering and aggregation, which adversely affects their utility as MR contrast agents. Further, at no time are the metal oxides removed from superparamagnetic fluid by precipitation or filtration; in fact, they cannot be so removed. In dilute concentrations, the metal oxides will pass through a 0.22 micron filter.

2. Because the material is never precipitated (after the initial formation of the iron oxide), acids or bases are not needed to resolubilize the iron oxide. Use of acids tends to dissolve iron oxides, yielding ferric ion which is toxic and must be removed prior to in vivo use. Strong bases are also poorly suited for use in the preparation of pharmaceutical solutions of superparamagnetic fluids. Strong bases can hydrolyze biological molecules attached to iron oxides such as proteins or polysaccharides. Amine-containing strong bases can react with polysaccharides in the well known Malliard reaction.

3. Changes in solvents, such as to citrate buffer, are accomplished by dialysis. Many other methods (such as that described in U.S. Pat. No. 4,001,288) of iron oxide preparation require removal of iron oxides from solution to accomplish changes in solvent, often using acid or base to resolubilize the precipitate.

4. The attachment of coating materials to the particles during the preparation permits a wide array of biologically active molecules such as antibodies, antigens, serum proteins or other materials to be attached. The attached biologically active molecule can serve to direct the superparamagnetic agent in vivo, as described in section 6.5.

6.4. Characteristics of Superparamagnetic Fluids

6.4.1. Magnetic Properties

The fluids produced by the methods described in section 6.3. are characterized by a high magnetic moment in a high magnetic field (generally, about 5 to about 90 EMU/gm of metal oxide) and a negligible magnetic moment in the absence of an applied field (i.e., a magnetic squareness of less than 0.1). Such behavior is characteristic of superparamagnetic particles.

FIG. 4 shows magnetic hysteresis loops for typical paramagnetic, superparamagnetic and ferromagnetic iron oxides. Magnetization was measured in a vibrating sample magnetometer with up to 6,000 Gauss, 25° C. At nigh magnetic fields, the superparamagnetic fluid of the invention is nearly as magnetic as ferromagnetic iron oxide and far more magnetic than the paramagnetic ferric oxyhydroxide. Also, the solutions of the invention are superparamagnetic rather than ferromagnetic, losing virtually all of their magnetic moment in the absence of an applied magnetic field. In fact, the superparamagnetic solutions of this invention are characterized by a saturation magnetization of 30 EMU/gm or greater, with the loss of more than 90% of this magnetism in the absence of a magnetic field.

6.4.2. Retention of Citrate and Stability of Superparamagnetic Fluids

The retention of citrate (from aqueous sodium, potassium, or ammonium citrate buffer) can be used to distinguish the superparamagnetic fluids of this invention from other iron oxides. Studies of citrate binding capacity of commercially available forms of iron oxides and ferric oxyhydroxides reveals that the iron oxides in the superparamagnetic fluids of this invention are capable of retaining nearly as much citrate as the paramagnetic (ionic) ferric oxyhydroxide, while gamma ferric oxide and magnetite cannot retain significant amounts of citrate. The inability of iron oxides to retain citrate, coupled with the ability of ferric oxyhydroxide to do so, strongly suggest that citrate does not adsorb to the surfaces of iron oxides prepared according to the method of this invention (see Section 6.3) through the usual chemical adsorption mechanism. The retention of anions like citrate by the superparamagnetic iron oxides of the invention indicates these materials have an ionic character similar to the ferric oxyhydroxides.

The stability of fluids of the invention is shown in FIGS. 5A and 5B where a superparamagnetic fluid made according to the procedure described in section 6.3. was subjected to autoclaving with and without citrate. Addition of 50 mM citrate stabilized a solution of 1.26M iron oxide, preventing the gelation of the material.

The stability of the oxyhydroxide solutions of iron (i.e., the superparamagnetic fluids) is related to the exchange of hydroxide for citrate ion. Both paramagnetic and superparamagnetic oxyhydroxides retain citrate in a similar fashion:

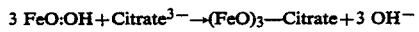

$$3\ FeO{:}OH + Citrate^{3-} \rightarrow (FeO)_3\text{---}Citrate + 3\ OH^-$$

Instead of trying to block the Van der Waals forces between neutral crystals with polymers, by attaching surfactants, or forming complexes, the general approach used by others in forming ferrofluids, the invention's superparamagnetic fluids are stabilized due to the ionic character of the iron oxide and the choice of appropriate anions.

The stable solutions of this invention comprise a metal concentration ranging from 0.05 to 5 molar and a citrate ion concentration of 0.001 to 0.1 moles of citrate/mole preferably 0.01 to 0.1 moles of citrate/mole of iron at a pH ranging from about 6 to about 10. As the concentration of iron in the solution is increased, the ratio of citrate/iron must also increase to yield the stability. Thus, they are compatible with physiological conditions.

The superparamagnetic fluids of the invention owe their stability in solution, not to their coating with polymers or surfactants, but to the existence of a cationic character of the iron oxide and its stabilization with anions such as citrate. In general, polymeric coatings, though they help stabilize iron oxides, are not sufficient to protect them against the rigors of autoclaving. In contrast, superparamagnetic fluids made according to the invention can be made omitting the polymer altogether and are highly stable.

6.4.3. Effectiveness as MR Contrast Agents

In evaluating magnetic materials as MR contrast agents, the ability of materials to shorten proton relaxation time can be more important than bulk magnetic properties such as magnetization. Since MR imaging works by determining the rates of two types of proton relaxations in various tissues and, by using variations in those relaxation rates, develops an image, the differences in proton relaxation times between the tissues must be sufficiently great to obtain a good quality image. As stated supra, MR contrast agents work by shortening proton relaxation time and, thus, increases the contrast and overall image quality. Two relaxation parameters termed spin-spin relaxation time ($T_1$) and spin-lattice relaxation time ($T_2$) are used in the generation of the MR image.

In experiments evaluating the effect of these materials as contrast agents, it was found that the superparamagnetic fluids have a much greater effect on both $T_1$ and $T_2$ than any commercially available iron compounds including chelated ferric ion, paramagnetic ferric oxyhydroxides, gamma ferric oxides, and superparamagnetic iron oxide clusters Seer U.S. Pat. No. 4,584,088. In fact, the material of the invention is remarkable in its ability to shorten proton relaxation. The materials prepared according to the invention are more potent enhancers of proton relaxation than either ferromagnetic materials or paramagnetic ferric oxyhydroxide. In addition, the highly dispersed state of the materials of the invention produces higher relaxivities than those characteristic of clustered materials (See 7.12 and Table III). The process, thus, yields superparamagnetic solutions optimized for their effects on proton relaxation time.

The high relaxivity (see Table III) of the materials of the invention is important to their pharmaceutical use as MR contrast agents, because it results in large effects on the MR image with small doses of iron. For example, superparamagnetic iron oxides made according to the invention can profoundly improve liver imaging at doses of 1 mg of iron per kilogram of rat, while the LD50 for the rat is greater that 250 mg of iron per kilogram.

6.5. Biodegradability

Both the superparamagnetic particles in the dispersoids and the metal oxides in the superparamagnetic fluids of the invention have been found to be biodegradable when administered in vivo (see Examples 7.6 and 7.15). In fact, iron, the predominant species in the dispersoids and fluids accumulate in the liver, where it is eventually catabolized and incorporated into the subject's hemoglobin. Thus, the dispersoids and fluids can be used in the treatment of anemia, and indeed, the fluids have been shown to be as effective as Imferon (a commercially used preparation for treatment of anemia in humans) in the restoration of normal hematocrit levels in anemic rats.

6.6. Directability

Both the superparamagnetic particles in the dispersoids and the metal oxides in the superparamagnetic fluids of the invention can be coated with various coating agents as described supra. The use of such coatings permits the attachment of various biological molecules to the imaging agents to permit targeting of various organs. For example, antibodies can be bound by a variety of methods including diazotization and attachment through a glutaraldehyde or carbodiimide coupling moiety (Examples of these coupling methods can be found in U.S. Pat. No. 4,628,037, which is incorporated herein by reference). Use of methods such as these permits maximum flexibility, as an antibody-directed superparamagnetic metal oxide can bind to a specific type of cell or tissue. This can permit an image to be generated which differentiates between the target and the surrounding tissue.

In addition to antibodies, other biological molecules which affect directability can also be attached to the particles as the particular application dictates. Some possible applications are listed below:

| Antibodies | Application |
| --- | --- |
| 1. Anti-heart myosin | Imaging infarcted area of heart |
| 2. Anti-fibrin | Image clot |
| 3. Anti-T-cells | Lymphoma |
| 4. Anti-CEA | Colonic tumor imaging |
| 5. Anti-melanoma antibodies | Melanoma imaging |
| 6. Anti-ovarian cancer antibodies | Ovarian cancer imaging |
| 7. IgG | Fc receptor delineation |

Carbohydrates

1. Bacterial lipopolysaccharides
2. Cellulose
3. Mucopolysaccharides
4. Starch
5. Modification of carbohydrate after synthesis, e.g., dextran coating made positively or negatively charged, diethylamino (DEAE) cellulose or carboxymethyl (CM) dextran.

| Hormones | Application |
| --- | --- |
| 1. Insulin | Insulin receptor status as in maturity onset diabetes |
| 2. Thyroid stimulating hormone | Thyroid disease |
| 3. Acetylcholine (or analogs) | Delineation of neural receptors |
| 4. Serum low density lipoprotein | Delineation of familial hyper cholesterolemia |
| 5. Hormone analogs including drugs | Delineation of endocrine system and receptors |
| 6. Serum transferrin | Transferrin receptors delineation |

6.7 Method for Extending the Serum Lifetime Of An MR Image Contrast Agent

To extend the lifetime of an MR imaging agent in the serum of a subject, if desired, it is necessary to prevent its absorption by the reticuloendothelial system (RES). It has been found that this can be accomplished by introducing to the subject a blocking agent which effectively competes with the imaging agent for binding the RES receptors responsible for removing the MR contrast agent from the bloodstream. There are a number of phagocytic receptors which function independently of each other. As a result, no single material is equally effective at blocking all the RES receptors and any blocking agent must be specific for the imaging agent. (See Davis et al. in "Polymeric Nanoparticles and Microspheres", Gurot, P. and Covreur, P., eds, (CRC Press, 1986) p. 180).

In the procedure, the subject is given a dose of paramagnetic iron oxide either prior to or along with the administration of the imaging agent. For the best results, the paramagnetic iron oxide should be as simlar to the agent as practical especially in particle size and coating. After a short time interval, generally 15–20 minutes during which time the paramagnetic material circulates in the bloodstream and binds to the RES receptors, the imaging agent is administered. By proper choice of the paramagnetic dosage, the lifetime of the imaging agent in the serum is greatly enhanced.

An excellent blocking agent for a superparmagnetic MR agent is a paramagnetic form of the same material. This is because the effectiveness of a blocking agent depends on whether a competition for receptors results; cell surface receptors bind materials in circulation prior to internalization. This internalization is termed pinocytosis (removal of liquids) or phagocytosis (removal of particles). If competition is created, which blocks removal of the superparamagnetic MR contrast agent, the removal of the contrast agent will be hindered. Because the RES receptors are specific and will bind substances of only one particular size or shape, this competition is best observed among materials which are physically similar. Since a paramagnetic particle can differ from a superparamagnetic particle only in its core magnetic properties and rather than its surface chemistry, a high degree of competition is inevitable and, thus, the paramagnetic material is a highly efficient blocking agent.

In a preferred embodiment, dextran-coated paramagnetic iron oxide is used as a blocking agent for dextran coated superparamagnetic iron oxide. This material is ideal as a blocking agent for dextran-coated superparmagnetic iron oxide contrast agents for the reasons below:

1. Its effect on proton relaxation is virtually undectectable by MR.
2. It can be made by the process used for superparamagnetic materials, but without the use of divalent iron, (which is required for the superparamagnetic product). The MR contrast agent and blocking agent are identical except for the fine structure of the iron- oxide which determines magnetism and its effect on proton relaxation. From the point of view of the cell surface receptor governing removal from circulation the superparmagnetic imaging agent and blocking agent are identical.
3. It is non-toxic in humans and has an established therapeutic use in the treatment of anemia. In fact, therapeutically approved paramagnetic dextran (Imferon) can be used as a blocking agent for the superparmagnetic MR contrast agents of the invention.

The extension of serum lifetime is of particular importance when MR measurements are used to confirm blood circulation (or lack thereof). In such measurements, the contrast agent is introduced parenterally and permitted to circulate. By measurement of $T_1$ and $T_2$, presence or absence of blood circulation can be determined. Such a procedure can be a valuable tool in the diagnosis of blood circulation disorders, and can be used to detect the flow of blood into areas where it is normally excluded, such as in strokes.

7. Examples

7.1. Preparation of Dextran-Coated Particles

To a solution of 500 mls of 0.28M $FeCl_3$, 0.16M $FeCl_2$ and 12.5% w/v dextran, (molecular weight 71,000 daltons from Sigma Chemical Company, Cat. #D1390) is added 500 mls 7.5% $NH_4OH$ over a 2 minute period. A black, magnetic solid forms comprised of large and small particles. The material is stirred for 5 minutes and then heated for 30 minutes at 70° C. The solution is centrifuged for 1500×g for 15 minutes to remove large particles, and the small particles are dialyzed against 10 gallons of $H_2O$ for three days, changing the water each day.

The resultant particles exhibit a diameter of about 1400 angstroms a measured by light scattering.

7.2. Preparation of Particles Coated with Bovine Serum Albumin

To a solution of 80 mls of 0.5% bovine serum albumin (BSA), 0.27M $FeCl_3$, and 0.16M $FeCl_2$, is added 80 mls of 7.5% $NH_4OH$. A black, magnetic solid forms comprised of particles. The mixture is allowed to stand for 5 minutes and then centrifuged at 1,500 ×g for 15 minutes to remove larger particles. The pellet is discarded and the supernatant placed in a dialysis bag and dialyzed against 3 changes of 10 gallons of distilled water. Larger particles are again removed by centrifugation as above and discarded. Particles are then concentrated by ultrafiltration using an XM-50 membrane and a stirred cell filtration device from Amicon Corporation, Lexington, MA.

The resultant particles exhibit a diameter of about 1730 angstroms as measured by light scattering.

7.3. Preparation of Uncoated Particles

One hundred milliliters of solution of 0.8M $FeCl_3$, 0.4M $FeCl_2$ and 0.4M HCl is added dropwise to 1000 ml of 2.4% $NH_4OH$ and mixed for 5 minutes. A black, magnetic solid forms comprised of easily visible particles. For particles to be visible, they must be larger than the wavelength of scattered light which is about 500 nm (0.5 microns). The particles are isolated by attracting them to a permanent magnet on the outside of the reaction vessel and the solution decanted. To the magnetic cake is added 55 mls of .50% triethylamine in water. Smaller particles are created. The mixture is dialyzed overnight against water which causes the large particles to reappear. Just enough triethylamine is then added to again create the smaller particles resulting from the addition of triethylamine. The particles are then filtered through a 0.2 micron filter indicating the final material is below this size.

7.4. Use of Particles In Liver Tumor Visualization

The effect of the dextran-coated particles of Section 7.1. on the image of a rat liver tumor is demonstrated in FIG. 2, which presents reproductions of five images obtained on a Technicare MR imager. The images in FIGS. 2A and 2B were obtained prior to the introduction of the imaging agent using different imager settings, in neither case can the tumor be clearly seen; FIGS. 2C and 2D are images of the same 15 rat liver and were obtained after a single 0.5 mg/kg dose of the Section 6.1. dextran-coated particle by intravenous injection through the tail vein, the tumor is easily seen and the overall size and shape can be gauged; in FIG. 2E the tumor is marked by cross-hairs to aid in visualization.

7.5. Comparative Effect of Superparamagnetic Particles And Ferromagnetic Particles On T2

Figure 1:
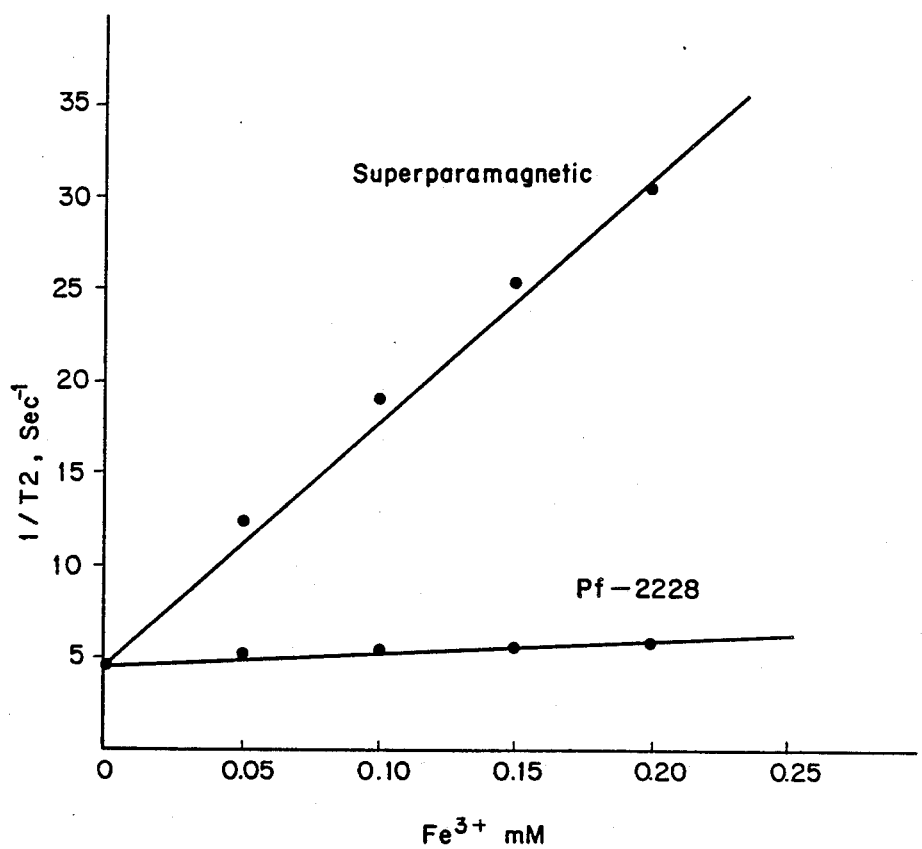
FIG. 1 is a graphical representation comparing the effect of ferromagnetic and superparamagnetic contrast agents on $T_2$.

FIG. 1 compares the $T_2$ of agar gel in the presence of dextran-coated particles (produced in Example 7.1.) and the ferromagnetic particle Pf-2228 (Pfizer). The relaxation times in the presence of varying concentrations of each particle were determined on an IBM PC-20 NMR spectrometer at 0.47 Tesla (4700 Gauss). It can clearly be seen that the superparamagnetic particle produces a much greater effect on $T_2$ than the ferromagnetic particle. Given the fact that superparamagnetic materials are much less magnetic than ferromagnetic materials, this result is quite surprising.

7.6. Biodegradability of Dextran-Coated Particles

A dispersion of uncoated superparamagnetic iron oxide particles in water was intravenously injected into Sprague-Dawley rats at a dosages 20, 37 and 243 micromoles Fe/kg of body weight. Periodically, the rats were sacrificed, and $T_2$ of the liver tissue was measured on an IBM PC-20 NMR Spectrometer. The results are presented in FIG. 3.

The data demonstrate that $T_2$ undergoes a marked drop rapidly after the injection, and then begins to recover slowly, presumably as the iron is metabolized. However, the effects are still detectable even two weeks after administration. Also, the effects are more marked with the higher dosages. Thus the particles have an extended lifetime in these organs. The liver and spleen are the major organs which store iron for incorporation into hemoglobin, and, indeed these materials are ultimately incorporated into the hemoglobin of the rat.

7.7. Biodistribution of BSA-Coated Particles

Six Sprague-Dawley rats of about 200 gm each were injected intravenously with 0.4 mg of the BSA-coated particle (produced in Section 7.2.) in distilled water. Two rats each were sacrificed at 90 minutes, 24 hours, and 7 days after injection and the relaxation times ($T_1$ and $T_2$ of various organs were measured on an IBM PC-20 NMR Spectrometer. The following results were obtained:

TABLE I
DISTRIBUTION OF BSA-COATED PARTICLE IN RAT ORGANS AND TISSUES

| Time After Injection | | Relaxation Times (msec) | | | |
|---|---|---|---|---|---|
| | | Liver | Spleen | Lung | Blood |
| Control | $T_1$ | 0.279 | 0.544 | 0.688 | 0.786 |
| $N^1 = 6$ | $T_2$ | 32 | 48.3 | 57 | 158 |
| 90 min | $T_1$ | 0.232 | 0.396 | 0.656 | 0.901 |
| N = 2 | $T_2$ | 20 | 22 | 56 | 136 |
| 24 hours | $T_1$ | 0.279 | 0.494 | 0.735 | 1.084 |
| N = 2 | $T_2$ | 22 | 44 | 68 | 155 |
| 7 days | $T_1$ | 0.268 | 0.572 | 0.712 | 0.972 |
| N = 2 | $T_2$ | 31 | 49 | 68 | 162 |

[1]N is the number of rats examined.

The data suggest that both the blood and the lung rapidly clear the magnetic material exhibiting nearly no effect on the relaxation times 50 minutes after the injection. The spleen demonstrates a moderately rapid recovery, exhibiting a substantial reduction in both $T_1$ and $T_2$ 90 minutes after the injection, but nearly no residual recovery rates. $T_1$ attains its original value after 24 hours, while $T_2$ remains substantially reduced after 24 hours and exhibits recovery after 7 days.

7.8. Comparative Biodistribution of Uncoated and Dextranized Particles

In this experimental series, the biodistribution of b three uncoated and four dextran-coated particles was examined. The uncoated agents were produced according to the procedure of Section 7.3., the dextran-coated particles were produced according to the procedure of Section 7.1. except that the molecular weight of the dextran used for the coating was varied (see TABLE II). Prior to each experiment, the contrast agents were dialyzed against distilled water and subsequently injected into separate groups of Sprague-Dawley rats in a distilled water carrier. The rats were periodically sacrificed and the relaxation times of the liver, spleen, and lung were determined on an IBM PC-20 NMR Spectrometer. Preprogrammed inversion recovery and Carr, Purcell, Meiboom, Gill pulse sequences were used to determine $T_1$ and $T_2$, respectively.

The results were as follows:

TABLE II

| Complex | Coating | Dose | Time After Dose | | Relaxation Times (msec.) | | |
|---|---|---|---|---|---|---|---|
| | | | | | Liver | Spleen | Lung |
| Control | — | None | — | $T_1$ | 0.27 | 0.54 | 0.717 |
| | | | | $T_2$ | 32 | 48 | 64 |
| AMI-12 | None | 24.2 μmoles/kg | 2.5 hr. | $T_1$ | 0.222 | 0.420 | 0.626 |
| | | | | $T_2$ | 22.7 | 26.0 | 45.8 |
| | | | 18 hr. | $T_1$ | 0.254 | 0.532 | 0.752 |
| | | | | $T_2$ | 29.6 | 42.9 | 68.2 |
| | | | 1 wk. | $T_1$ | 0.239 | 0.528 | 0.730 |
| | | | | $T_2$ | 31.6 | 43.8 | 72.0 |
| | | | 2 wk. | $T_1$ | 0.240 | 0.462 | 0.702 |
| | | | | $T_2$ | 29.4 | 35.5 | 79.5 |
| AMI-13 | None | 24.6 μmoles/kg | 2.5 hr. | $T_1$ | 0.221 | 0.424 | 0.672 |
| | | | | $T_2$ | 16.9 | 28.0 | 65.2 |
| | | | 18 hr. | $T_1$ | 0.218 | 0.386 | 0.802 |
| | | | | $T_2$ | 18.8 | 29.0 | 80.8 |
| | | | 1 wk. | $T_1$ | 0.236 | 0.443 | 1.753 |
| | | | | $T_2$ | 26.0 | 38.5 | 80.4 |
| | | | 2 wk. | $T_1$ | 0.236 | 0.493 | 0.722 |
| | | | | $T_2$ | 28.2 | 43.8 | 80.8 |
| AMI-14 | None | 25.4 μmoles/kg | 2 hr. | $T_1$ | 0.238 | 0.470 | 0.706 |
| | | | | $T_2$ | 20.8 | 31.8 | 72.4 |
| | | | 18 hr. | $T_1$ | 0.238 | 0.436 | 0.750 |
| | | | | $T_2$ | 20.4 | 34.7 | 69.6 |
| | | | 1 wk. | $T_1$ | 0.216 | 0.522 | 0.755 |
| | | | | $T_2$ | 26.7 | 41.7 | 80.4 |
| | | | 2 wk. | $T_1$ | 0.227 | 0.452 | 0.698 |
| | | | | $T_2$ | 24.8 | 43.6 | 78.7 |
| AMI-15 | Dextran 9,000 | 36.8 μmoles/kg | 4 hr. | $T_1$ | 0.238 | 0.300 | 0.672 |
| | | | | $T_2$ | 17.8 | 19.4 | 56.4 |
| | | | 24 hr. | $T_1$ | 0.253 | 0.387 | 0.740 |
| | | | | $T_2$ | 21.1 | 26.4 | 73.2 |
| | | | 1 wk. | $T_1$ | 0.219 | 0.485 | 0.766 |
| | | | | $T_2$ | 25.6 | 36.7 | 78.1 |
| | | | 2 wk. | $T_1$ | 0.258 | 0.523 | 0.718 |
| | | | | $T_2$ | 28.7 | 39.1 | 69.9 |
| AMI-16 | Dextran 17,900 | 32.4 μmoles/kg | 4 hr. | $T_1$ | 0.248 | 0.302 | 0.678 |
| | | | | $T_2$ | 18.8 | 16.5 | 56.2 |
| | | | 24 hr. | $T_1$ | 0.238 | 0.384 | 0.703 |
| | | | | $T_2$ | 19.9 | 24.9 | 71.6 |
| | | | 1 wk. | $T_1$ | 0.197 | 0.470 | 0.725 |
| | | | | $T_2$ | 25.3 | 37.1 | 74.6 |
| | | | 2 wk. | $T_1$ | 0.258 | 0.525 | 0.731 |
| | | | | $T_2$ | 28.9 | 44.8 | 73.3 |
| AMI-17 | Dextran 35,600 | 33.1 μmoles/kg | 4 hr. | $T_1$ | 0.244 | 0.318 | 0.674 |
| | | | | $T_2$ | 16.0 | 17.4 | 54.4 |
| | | | 24 hr. | $T_1$ | 0.247 | 0.388 | 0.690 |
| | | | | $T_2$ | 20.2 | 22.9 | 76.4 |
| | | | 1 wk. | $T_1$ | 0.214 | 0.500 | 0.696 |
| | | | | $T_2$ | 24.3 | 44.0 | 76.0 |
| | | | 2 wk. | $T_1$ | 0.244 | 0.562 | 0.726 |
| | | | | $T_2$ | 28.6 | 48.6 | 70.6 |
| AMI-18 | Dextran 249,000 | 39.2 μmoles/kg | 4 hr. | $T_1$ | 0.228 | 0.237 | 0.526 |
| | | | | $T_2$ | 20.0 | 17.7 | 58.6 |
| | | | 24 hr. | $T_1$ | 0.238 | 0.354 | 0.654 |
| | | | | $T_2$ | 21.0 | 22.0 | 68.2 |
| | | | 1 wk. | $T_1$ | 0.235 | 0.492 | 0.645 |
| | | | | $T_2$ | 31.4 | 36.1 | 71.3 |
| | | | 2 wk. | $T_1$ | 0.240 | 0.52 | 0.748 |
| | | | | $T_2$ | 31.0 | 39.8 | 71.3 |

As before, the data suggest that the contrast agents are rapidly cleared from the lung, and are longer lived in the spleen and the liver. Additionally, it can be seen that the dextran-coated particles are cleared less rapidly than the uncoated ones, exerting a significant effect on the $T_2$ values of the liver and spleen for about one week.

7.9. Preparation of Superparamagnetic Fluids Containing Uncoated Metal Oxide

7.9.1 Preparation of Superparamagnetic Iron Oxide

A solution of 0.25M ferrous chloride and 0.5M ferric chloride (600 ml) was poured into a solution., of 5M NaOH (600 ml). A black magnetic oxide precipitate was formed. This precipitate was washed repeatedly by base and decanted until a pH of about 9 was achieved.

7.9.2 Disperson and Oxidation

In a beaker, 400 ml of magnetic oxide (about 15 grams) from Section 7.9.1 and 25 ml of glacial acetic acid were mixed. A sonic probe was placed in the beaker and the solution was sonicated at high intensity for 2 minutes. The sonic probe was then remove and the solution centrifuged at 1,000×g for 20 minutes. The pellet was discarded and the supernatant liquid was retained.

7.9.3 Transfer to Citrate Buffer

The supernatant, from Section 7.9.2, was dialyzed against ammonium citrate buffer by use of a hollow fiber dialyzer/concentrator, model DC 2 (AMICON Corp. Danvers, MA). The ammonium citrate buffer is 10 mM citrate, adjusted to pH 8.2 with $NH_4OH$. The result is an autoclavable, homogeneous supermagnetic fluid.

7.10. Preparation of an Aqueous, Stable Superparamagnetic Fluid Containing Metal Oxide With Dextran Attached

7.10.1 Synthesis of Iron Oxide

Five liters of a solution containing 755 g $FeCl_3$ $6H_2O$ and 320 g $FeCl_2$ $4H_2O$ was added slowly to 5 liters of 16% $NH_4OH$ containing 2500 gm dextran (MW=10-15,000). The iron salt solution was added over 5 minutes during which time the base was vigorously stirred during addition.

A black magnetic slurry was formed.

7.10.2. Dispersion, Oxidation and Heating

The 10 liters of slurry (from Section 7.10.1) was pumped through a continuous flow sonicator connected to a 100° C. heating coil and cooling coil apparatus as indicated in FIG. 6. The pumping rate was about 0.4 liters per minute and pumping was continued for about 30 minutes. The resultant solution was subsequently centrifuged and the precipitated pellet was discarded.

7.10.3. Removal of Unreacted Dextran, Transfer to Citrate Buffer and Sterilization The supernatant (from Section 7.10.3) was diluted to a total volume of 20 liters with deionized, sterile water and the resultant solution was dialyzed as in Example 7.9, except that a larger dialyzer concentrator < the DC 10, was used. The dialyzer cartridge had a 100,000 dalton molecular weight cutoff, permitting removal of dextran. Ultrafiltration was accomplished in a noncontinuous fashion, reducing the volume from 20 to 5 liters and adding 16 liter volumes of solution. Five volumes of 16 liters of deionized, distilled water were added.

Sodium citrate was then added as 1M citrate buffer stock and the solution was dialyzed as in Example 7.9. The resultant citrate was adjusted to pH 6.5 with NaOH before autoclaving. The citrate to iron ratio was between 0.01 and 0.1 citrate/Fe in the final solution. (For example, for an iron concentration of 1.26M, 0.04M citrate was present. The magnetic fluid was bottle d and autoclaved (121° C, 30 minutes). The result is a sterile homogenous magnetic fluid as shown in FIG. 5.

7.11. Preparation of an Aqueous Stable Superparamagnetic Fluid Containing Metal Oxide with Silane Attached

7.11.1 Preparation of an Iron Oxide

A solution of 0.25M ferrous chloride and 0.5M ferric chloride (600 ml) was poured into a solution of 5 M NaOH (600 ml). A black magnetic oxide precipitate formed which was repeatedly washed by base and decanted until a pH of about 9 was achieved.

7.11.2. Dispersion, Oxidation and Silanization

In a beaker 400 ml of magnetic oxide (from Section 7.11.1., about 15 grams) and 25 ml of glacial acetic acid were mixed. A sonic probe was placed in the beaker and the solution was sonicated at high intensity for 2 minutes. The sonic probe was then removed and 30 ml of N-2-aminoethyl-3-aminopropyltrimethoxysilane was added. The resultant mixture was then sonicated as before. The magnetic solution was subsequently added to 200 ml of glycerol at 50° C. The temperature was raised to 105° C. and the water was evaporated.

Due to the use of sonication, the material made is far smaller than that described in U.S. Pat. No. 4,554,088. Due to its small size, it cannot be manipulated with hand held magnets. The glycerol dehydration step is from U.S. Pat. No. 4,554,088 herein incorporated by reference..

7.11.3. Removal of Unreacted Silane and Transfer to Citrate Buffer

The glycerol slurry, from Section 7.11.2, was added to about 800 ml of water. Large aggregates of magnetic particles were removed by centrifuging the slurry at 1,000 ×g for 20 minutes. The supernatant was then dialyzed against citrate buffer in a hollow fiber dialysis device as in Example 7.9.3.

7.12. Effect of the Superparamagnetic Fluid on Proton Relaxation time

The effects of materials on an in vivo MR image can be evaluated through the use of a magnetic resonance spectrometer. In this study, an IBM-PC 20 instrument which measures $T_1$ and $T_2$ at 25° C., 0.47 Tesla and 20 MHz was used. Enhancement of proton relaxation can be quantified by taking the slope of a plot of $1/T$, the reciprocal of the relaxation time, versus the concentration of contrast agent. The plot is generally linear, with the slope being termed the relaxivity and denoted R1 or R2. Relaxivity has units of $M^{-1} sec^{-1}$. Higher relaxivity values indicate that material is more potent per mole of iron at decreasing relaxation times of protons and, thus, is a more potent contrast again. Relaxivities for a number of different forms of magnetic materials were determined. The following materials were examined:

Superparamagnetic fluid of the invention: A dispersed fluid containing superparamagnetic crystals of iron oxide prepared as described in Example 7.10. The magnetization curve of this material is presented in FIG. 4.

$Fe_2O_3$: A ferromagnetic gamma ferric oxide used for data recording. This material was obtained from Pfizer Corp., Minerals, Pigments and Metals Division, catalogue #2228.

Cluster: A silanized cluster of superparamagnetic iron oxide with tens to hundreds of crystals packed into micron-sized particles. This material was made according to U.S. Pat. No. 4,554,088.

FeO:OH: a paramagnetic, ferric oxyhydroxide used in the treatment of anemia. It was obtained from Fisons Corporation and is sold under the trade names of Proferdox (Fisons corporation) or Imferon (Merril Dow Inc.)

$Fe^{3+}$/DTPA: a soluble complex of ferric ion and diethylenetriaminepentacetic acid (DTPA). (The data for this material is from Lauffer at al, J. Comp. Assit. Tomog. 9(3), 431 (1985)).

The results were as follows:

TABLE III

| EFFECT OF DIFFERENT FORMS OF IRON ON PROTON RELAXATION TIME | | |
|---|---|---|
| Material | R1 ($M^{-1} \times sec^{-1}$) | R2 ($M^{-1} \times sec^{-1}$) |
| superparamagnetic fluid | $4 \times 10^{+4}$ | $1.6 \times 10^{+5}$ |
| gamma $Fe_2O_3$ | 100 | $7.2 \times 10^{+3}$ |
| FeO:OH | 0 | 60 |
| Cluster | $2 \times 10^{+3}$ | $3 \times 10^{+4}$ |
| $Fe^{3+}$/DTPA | $0.73 \times 10^{+3}$ | $0.85 \times 10^{+3}$ |

Briefly, as the high values R1 and R2 indicate, material of the invention is remarkable in its ability to shorten proton relaxation times For comparison, the value of R2 for ferromagnetic dextran magnetite is $1.7 \times 10^{+4} M^{-1} sec^{-1}$ [Ohgushi et al., J. Mag Res. 29, 599 (1978)]. This is the highest literature value for R2 of which the authors are aware. The materials prepared according to the invention are more potent enhancers of proton relaxation time than either ferromagnetic materials or paramagnetic ferric oxyhydroxides.

Additionally, well dispersed materials, such as those of the invention, have higher relaxivities than clustered materials. Thus, the process of the invention yields superparamagnetic solutions optimized for their effects on proton relaxation.

7.13. Bulk Magnetic Properties of Superparamagnetic Fluids

Magnetic hysteresis loops were obtained for the samples of the invention superparamagnetic fluid, gamma $Fe_2O_3$ (ferromagnetic), and FeO:OH (paramagnetic) examined in Example 7.12, using a commercial vibrating sample magnetometer with fields up to 6000 Gauss, 25° C.. The results are presented in FIG. 4.

Briefly, at high magnetic fields, the superparamagnetic fluid of the invention is nearly as magnetic as ferromagnetic iron oxide and far more magnetic than the paramagnetic ferric oxyhydroxide, showing a high magnetic saturation. The fluids of the invention are superparamagnetic rather than ferromagnetic, losing virtually all of their magnetic moment in the absence of an applied magnetic field.

7.14. Retention of Citrate

The retention of $^{14}C$ citrate upon dialysis can be used to distinguish various forms of iron oxide as shown in Table IV. All iron oxides were initially dialyzed against a buffer of 1 mM Tris-Cl, pH 8 before use. Equilibrium dialysis was then performed to determine fraction of citrate retained The concentrations of iron and citrate were 17.8 and 2.6 mM, respectively. The superparamagnetic fluids of the invention retain amounts of citrate similar to commercially available ferric oxyhydroxides indicating that the iron in both preparations is in a similar chemical form. Commercially available forms of iron oxide, such as gamma $Fe_2O_3$ or $Fe_3O_4$, do not retain significant amounts of citrate (the gamma $Fe_2O_3$ was the same as that used in Examples 7.12 and 7.13 while the $Fe_3O_4$ was purchased from Fisher Scientific Inc). The inability of these commercially available iron oxides to retain citrate, coupled with the ability of ferric oxyhydroxide to do so, strongly suggests that citrate does not absorb to iron oxide surfaces through the usual chemical adsorption mechanism. The retention of citrate by the superparamagnetic iron oxides of the invention indicates these materials have an ionic character similar to the ferric oxyhydroxides.

TABLE IV

RETENTION OF CITRATE BY SOLUTIONS WITH DIFFERENT IRON OXIDES

| Material | Citrate Retained per Iron (mole/mole) |
|---|---|
| FeO:OH | 0.026 |
| Invention | 0.019 |
| gamma $Fe_2O_3$ | 0.0028 |
| $Fe_3O_4$ | 0.0018 |

7.15. Stability of Superparamagnetic Fluids

Superparamagnetic fluids made according to Example 7.10 were subjected to autoclaving with various concentrations of citrate. At iron concentration of 1.26M, various concentrations of ammonium citrate, pH8 were added, and the resulting solutions heated 1 hour at 121° C. The results are presented in FIGS. 5A and 5B. The 6 vials of FIG. 5B contained, as shown, citrate concentrations of 100, 50, 25, 15, 10 and 5 mM citrate, respectively. The vials were upright during autoclaving but were placed horizontally for the photograph. With the vials lying horizontally, the presence of gelled material is evident when the upper portion of the vial is translucent. The fully blackenend vials (citrate concentrations between 15 and 100 mM) indicate a solution of superparamagnetic materials was maintained. The two vials on the right (citrate concentration of 5 and 10 mM) show the formation of a gel. FIG. 5A further shows the characteristic gel obtained without citrate, or with inadequate citrate (5 and 10 mM citrate).

7.16. Biodegradability of Superparamagnetic Fluids

Paramagnetic ferric oxyhydroxides are biodegradable and have long been used for the treatment of anemia. Therefore, the biodegradability of the invention's superparamagnetic fluids was compared with the paramagnetic ferric oxyhydroxides. The ability of both iron preparations to reverse anemia in rats was utilized as a model. The paramagnetic ferric oxyhydroxide was Imferon, and has dextran attached. The supermagnetic fluid also had dextran attached and was produced as described in Example 7.10.

Weanling rats were divided into four groups of five rats each. Rats in group 1 received a chow containing iron and were sacrificed at weeks 5, 6, 7 and 8 to allow establishment of normal iron (hematocrit) levels in rat tissues. Rats in groups 2, 3 and 4 received an iron deficient diet. Rats in group 2 were also sacrificed at weeks 5, 6, 7, and 8 to allow establishment of normal iron levels in rat tissues. Rats in groups 2, 3 and 4 received an iron deficient diet. After receiving the low iron diet for 5 weeks, rats in groups 3 and 4 received intravenous (tail vein) injections of iron to reverse their anemia and restore normal levels. Rats in group 3 received Proferdex, while those in group 4 received the dextranized superparamagnetic fluid. Rats receiving iron were injected with a single dose of 30 mg of iron per kilogram, a sufficient dose to reverse their anemia. The results are presented in Table V.

TABLE V

REVERSAL OF ANEMIA WITH SUPERPARAMAGNETIC IRON OXIDE PARTICLES

| | Hematocrit (1% red cells in whole blood) | | | | | | | |
|---|---|---|---|---|---|---|---|---|
| | week 5 | | week 6 | | week 7 | | week 8 | |
| | avg | sd | avg | sd | avg | sd | avg | sd |
| chow | 45.1 | 1.4 | 45.2 | 0.5 | 46.7 | 0.9 | 47.0 | 0.8 |
| low Fe | 28.5 | 2.6 | 29.5 | 2.1 | 32.7 | 1.2 | 34.8 | 2.3 |
| Imferon | | | 43.1 | 1.9 | 42.8 | 1.3 | 46.3 | 1.2 |
| Invention | | | 44.3 | 2.3 | 42.7 | 1.1 | 47.6 | 1.6 |

It can be seen that the invention's superparamagnetic iron oxide restores normal hematocrit levels in rats as well as the paramagnetic preparation, Imferon.

7.17. Summary of Superparamagnetic Fluid Properties

The properties of the superparamagnetic fluids of the invention compared with solutions made with other types of ferric oxide are summarized Table VI:

TABLE VI

SUMMARY OF PROPERTIES OF AQUEOUS SOLUTIONS OF VARIOUS FERRIC OXIDES

| | Mag. Saturation (FIG. 4) | MR Relaxivity (Table II) | Biodegradability (Table V) | Citrate retention (Table IV) |
|---|---|---|---|---|
| FeO:OH | low | none | high | high |
| gamma $Fe_2O_3$ | high | some | | low |
| Invention | high | high | high | high |

Thus, the superparamagnetic fluids of this invention posess a unique combination of magnetic, biological and anion retaining properties.

7.18. Extension of the Serum Lifetime of Dextran Coated Superparamagnetic Iron Oxide Particles To assess the effectiveness of dextran-coated paramagnetic iron oxide as a serum lifetime extender for dextran-coated superparamagnetic iron oxide particles, a comparative study was conducted.

In both trials, a rat of about 300 g was injected with 1 mg Fe/kg body weight of dextran-coated superparamagnetic metal oxide produced as described in Example 7.1. However, in one trial, the rat was also injected with 2.5 mg Fe/kg dextran-coated paramagnetic iron oxide (produced following the procedure described in Example 7.1 except that no divalent salt was used) 15 minutes prior to receiving the superparamagnetic material. The $T_2$ of the subject's blood was measured periodically over the subsequent 3 hours. The results are present in FIG. 7.

Briefly, in both trials, the blood $T_2$ dropped dramatically within 5 minutes after the superparamagnetic material was added. However, the value rapidly returned to normal in the rat which did not receive the superparamagnetic material, presumably due to absorption of the agent by the reliculoendothelial system (RES). In contrast, when the paramagnetic agent was used the $T_2$ depression is dramatically extended. This is due to a competition between the superparamagnetic and the paramagnetic material for RES receptors, greatly expanding the lifetime of the superparamagnetic agent.

It is apparent that many modifications and variations of this invention as hereinabove set forth may be made without departing from the spirit and scope thereof. The specific embodiments described are given by way of example only and the invention is limited only by the terms of the appended claims.

What is claimed is:

1. A method for obtaining an in vivo MR image of an organ or tissue of an animal or human subject which comprises (a) administering to such animal or human subject an effective amount of a contrast agent in a physiologically acceptable carrier, which contrast agent comprises a biodegradable superparamagnetic metal oxide, said biodegradable superparamagnetic metal oxide being characterized by biodegradation in such subject within about 2 weeks or less after administration, as evidenced by a return of the proton relaxation rates of said organ or tissues to preadministration levels; and (b) obtaining an MR image from such subject.

2. The method of claim 1 in which said biodegradable metal oxide is associated with a polymeric substance.

3. The method of claim 2 in which said polymeric substance is a polysaccharide.

4. The method of claim 1, 2, or 3 in which said metal is iron.

* * * * *